(12) United States Patent
Ferenc et al.

(10) Patent No.: US 6,500,444 B1
(45) Date of Patent: Dec. 31, 2002

(54) CONTINUOUSLY FRAGRANCE-EMITTING DRY OR WET WIPE FABRIC ARTICLE AND METHOD FOR PREPARING SAME

(75) Inventors: Dionisio Ferenc, Buenos Aires (AR); Marcos Angelini, Hammersmith (GB); Elena Susana Novas, Florida (AR); Leonardo Oscar D'Ascanio, Buenos Aires (AR)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/468,132

(22) Filed: Dec. 21, 1999

(51) Int. Cl.[7] .............................. A61K 9/70; A61L 15/16
(52) U.S. Cl. ...................... 424/404; 424/402; 424/400; 424/443; 424/447
(58) Field of Search .................. 424/404, 402, 424/403, 443, 447; 428/364, 372, 324

(56) References Cited

U.S. PATENT DOCUMENTS

| | | | | |
|---|---|---|---|---|
| 2,830,011 A | * | 4/1958 | Parker et al. | 167/84 |
| 3,567,118 A | | 3/1971 | Shephard et al. | 239/6 |
| 3,567,119 A | * | 3/1971 | Wilbert et al. | 239/6 |
| 4,713,291 A | | 12/1987 | Sasaki et al. | 428/373 |
| 4,917,920 A | * | 4/1990 | Ono et al | 427/389.9 |
| 5,156,843 A | * | 10/1992 | Leong et al. | 424/411 |
| 5,902,757 A | * | 5/1999 | Stern et al. | 442/324 |
| 6,207,274 B1 | * | 3/2001 | Ferenc et al. | 428/364 |

FOREIGN PATENT DOCUMENTS

| | | | |
|---|---|---|---|
| EP | 908549 | 4/1999 | ............ D04H/3/14 |
| WO | 9803713 | 1/1998 | .......... D04H/13/00 |
| WO | 9921507 | 5/1999 | |

* cited by examiner

Primary Examiner—Thurman K. Page
Assistant Examiner—Rachel M. Bennett
(74) Attorney, Agent, or Firm—Arthur L. Liberman

(57) ABSTRACT

Described is a permanently and continuously fragrance-emitting dry or wet wipe laminar fabric article comprising a non-woven fabric lamina having woven therethrough and substantially throughout at least a major portion of the lamina surface at least one continuous fragrance-containing thermoplastic, substantially water-insoluble fiber, which controllably and continuously releases fragrance at least for the time period during which the fabric article is in use. Such fragrance may also have antimicrobial properties. Optionally, one or more antimicrobial substances may also be releasably contained in the fiber containing the fragrance or in a fiber apart therefrom. The fabric article optionally contains additional fragrance and/or antimicrobial agent absorbed in or adsorbed on the non-woven fabric lamina. Also described is a process for preparing the permanently fragrance-emitting dry or wet wipe laminar fabric article by means of (a) creation of a non-woven fabric lamina optionally containing fragrance which may also have antimicrobial properties and/or at least one antimicrobial agent; (b) creation of a fragrance-containing polymeric fiber which, optionally, also contains at least one antimicrobial agent; and (c) weaving the fragrance-containing fiber through the non-woven fabric lamina substantially across at least a major portion of the surface area of the non-woven fabric lamina.

26 Claims, 19 Drawing Sheets

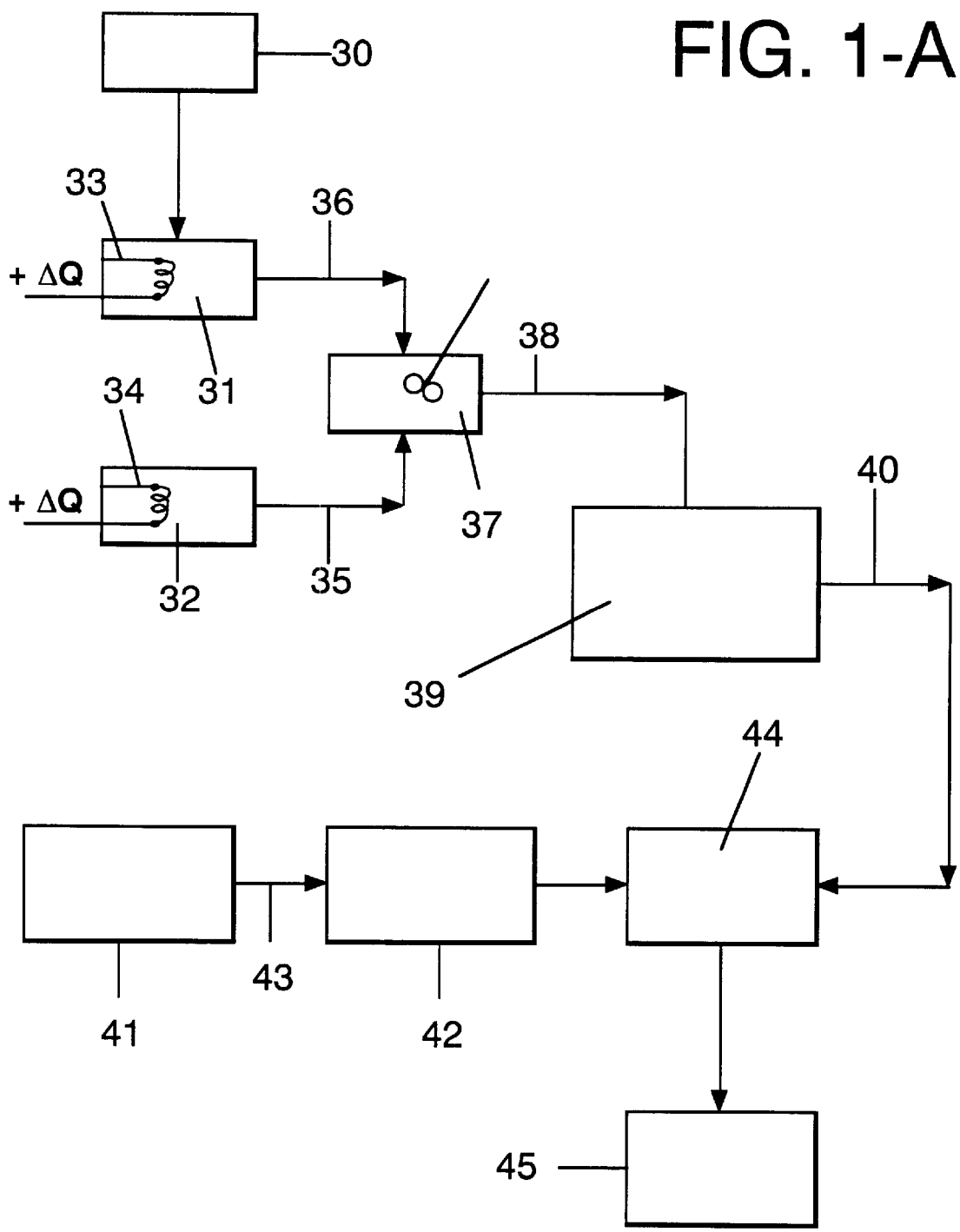
FIG. 1-A

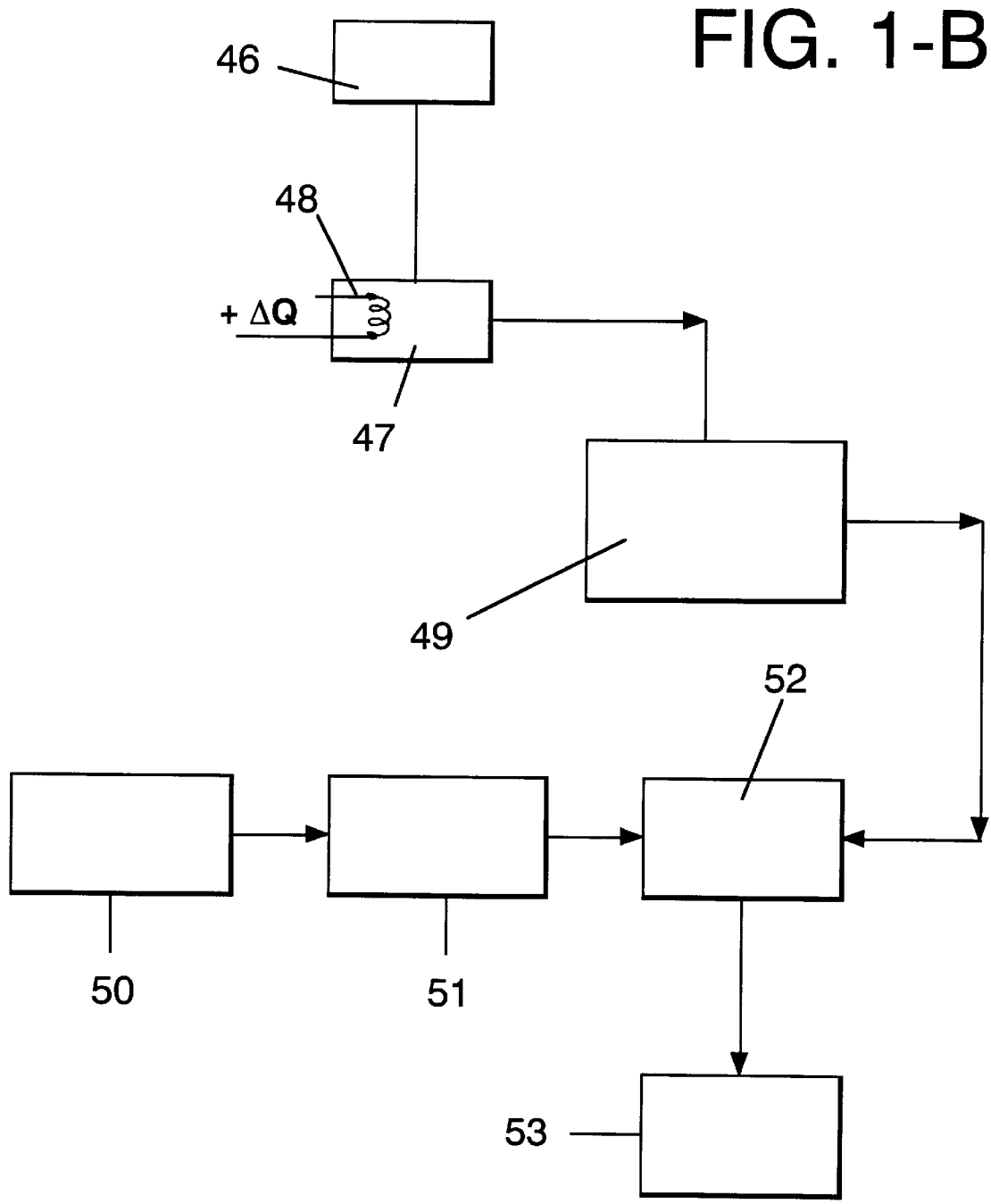
FIG. 1-B

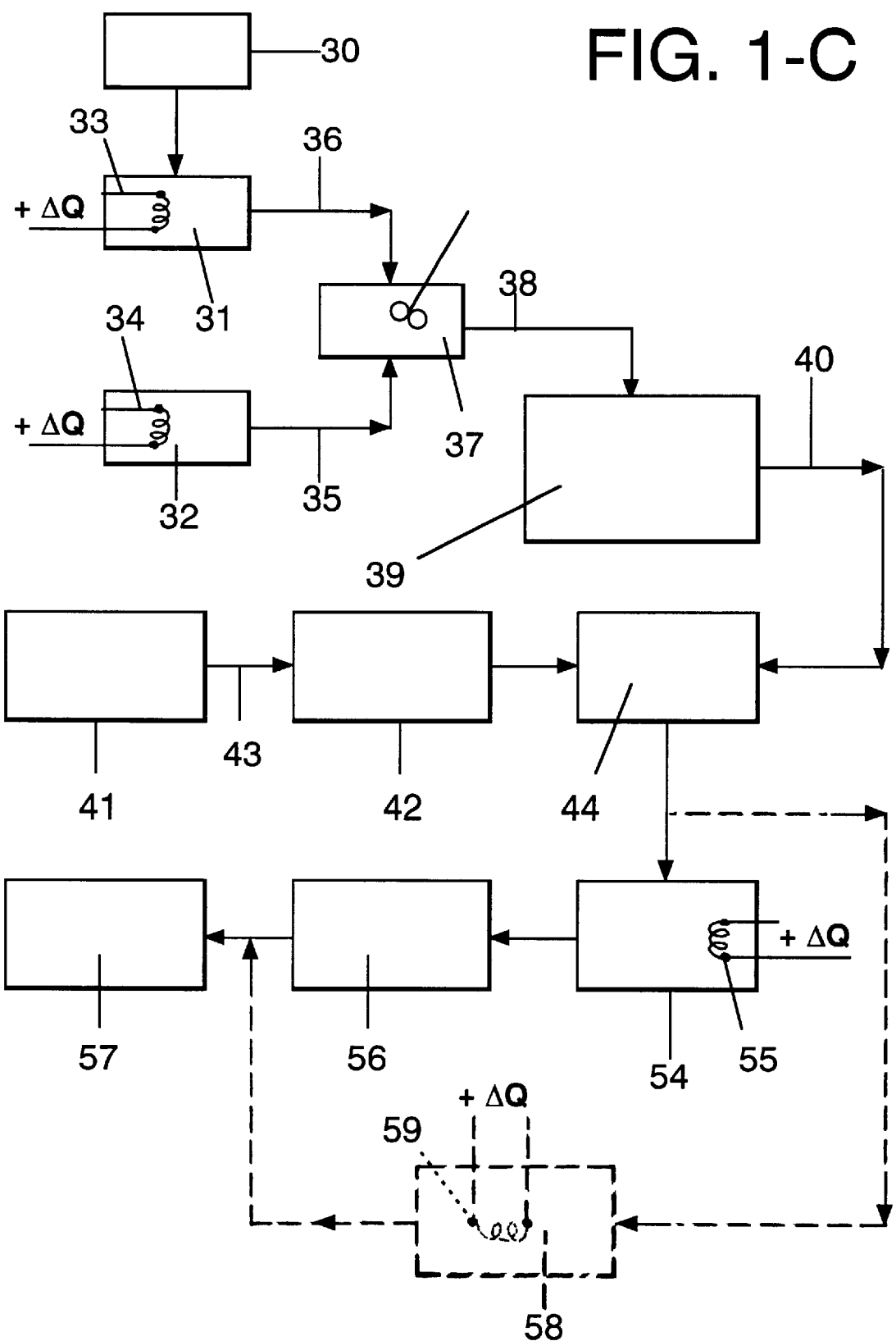
FIG. 1-C

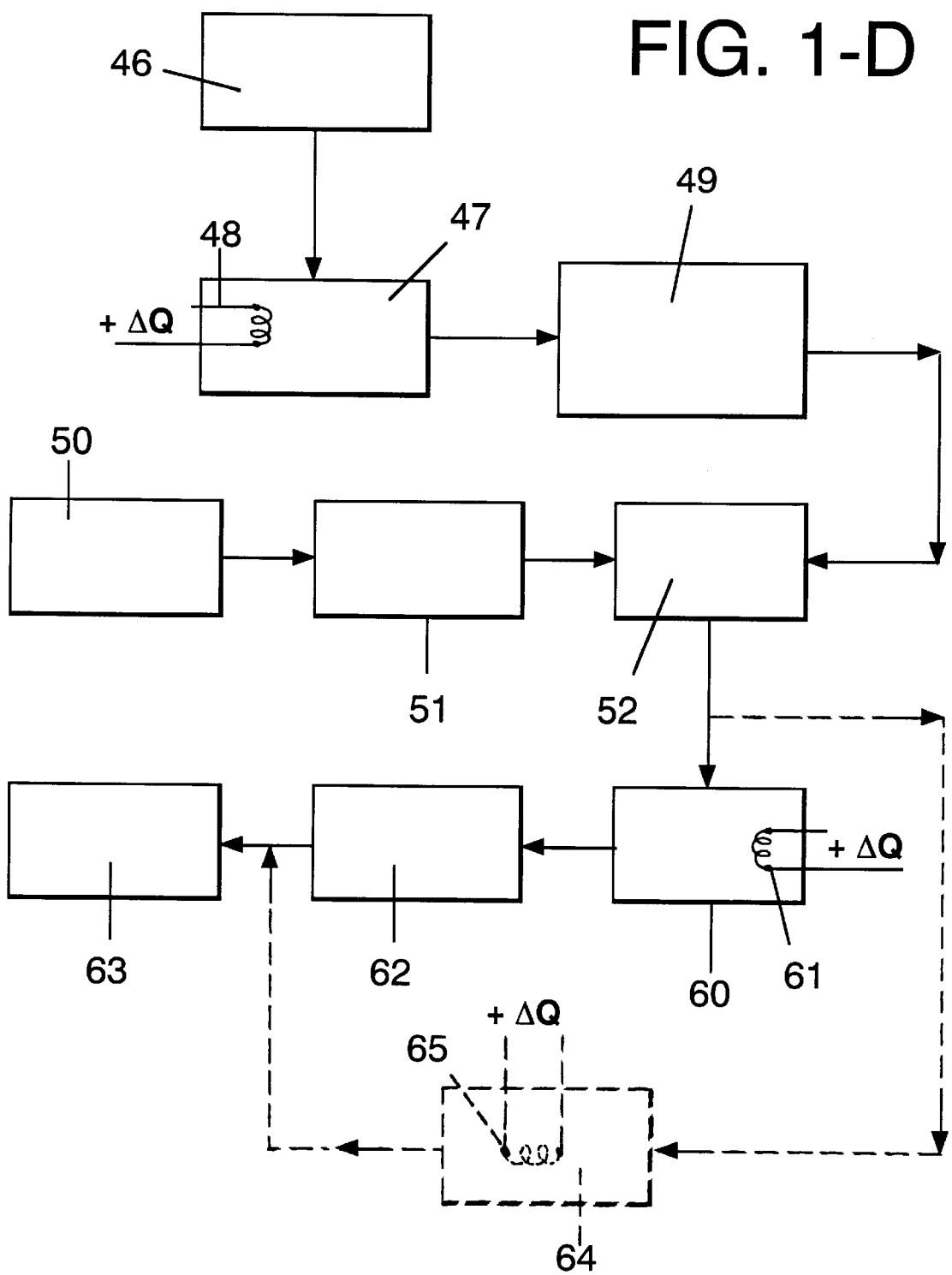
FIG. 1-D

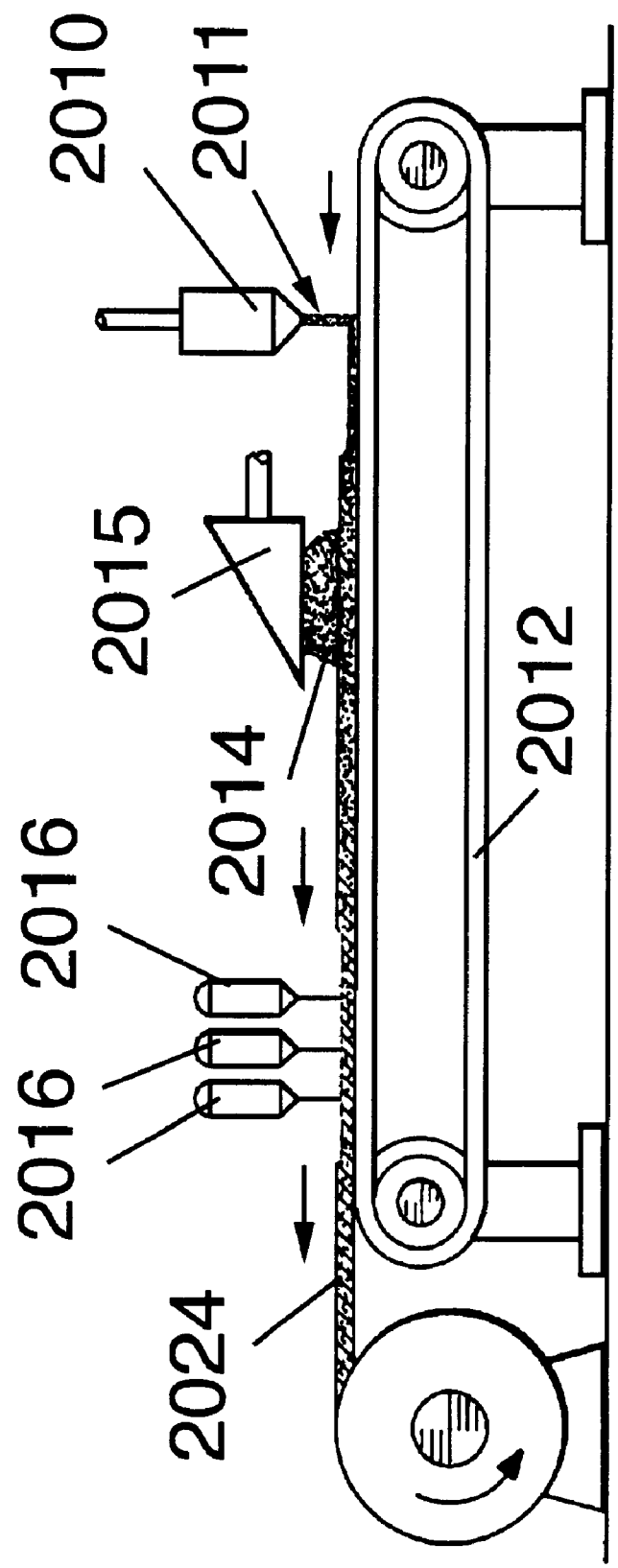

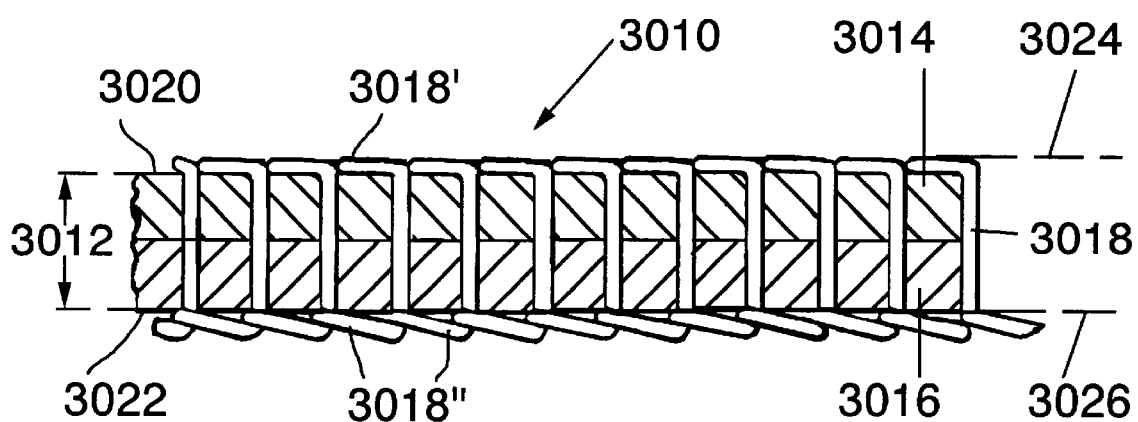
FIG. 1-F
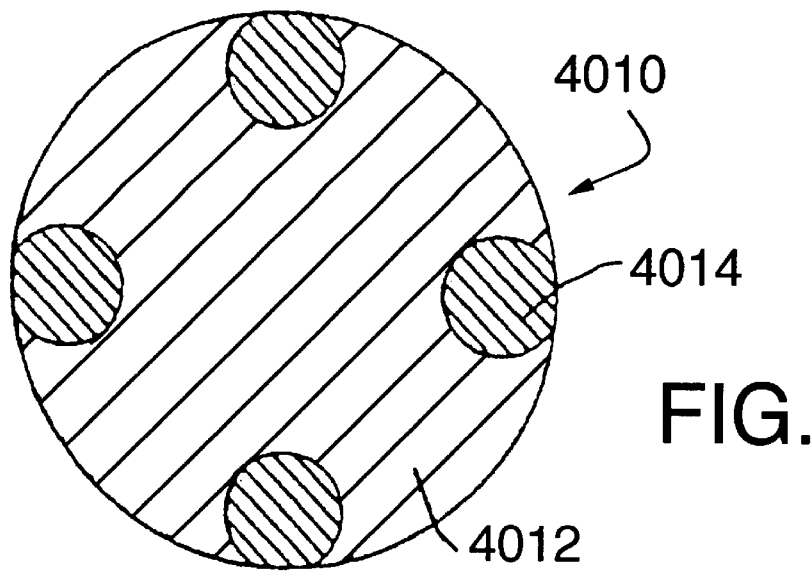
FIG. 1-G

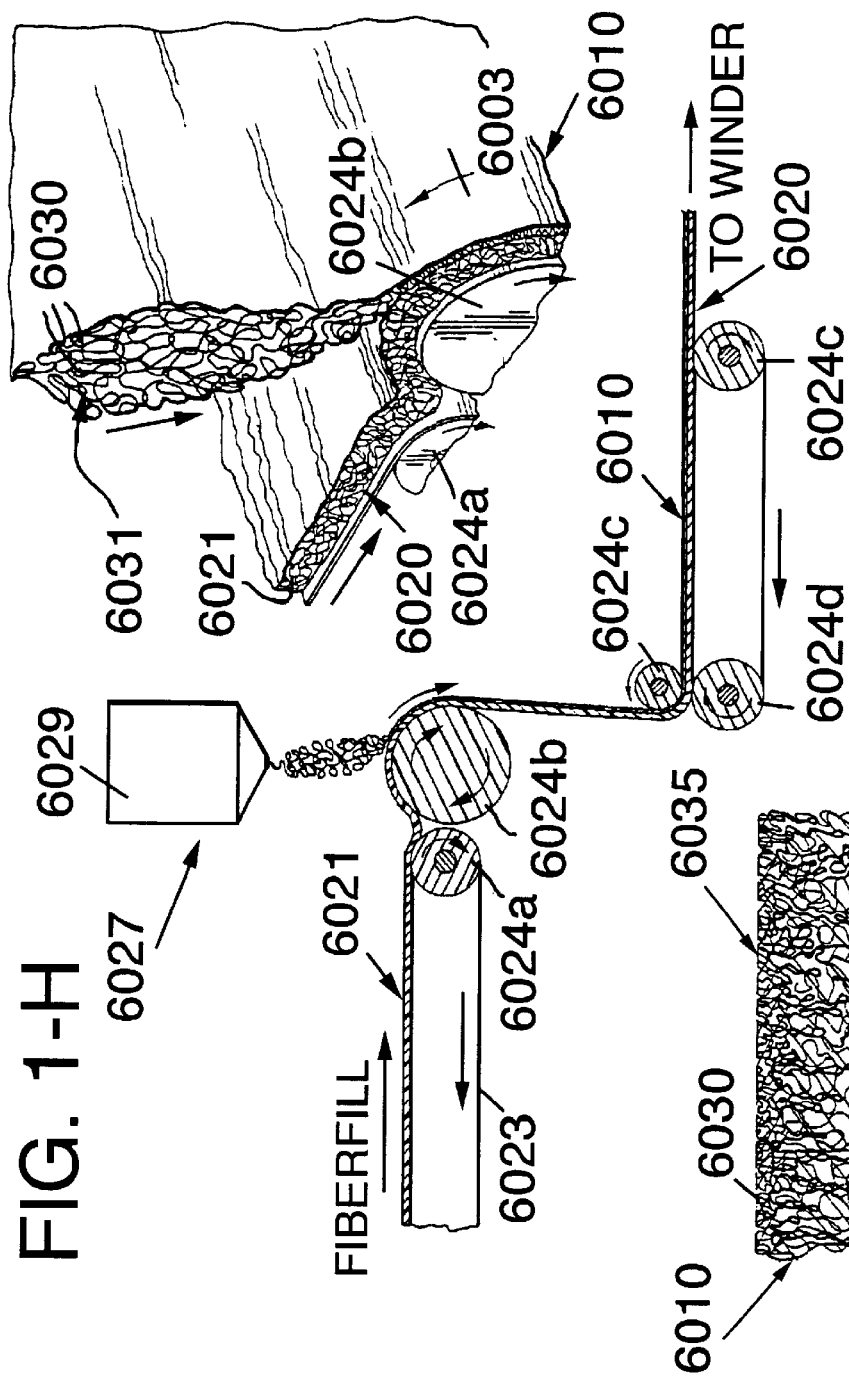

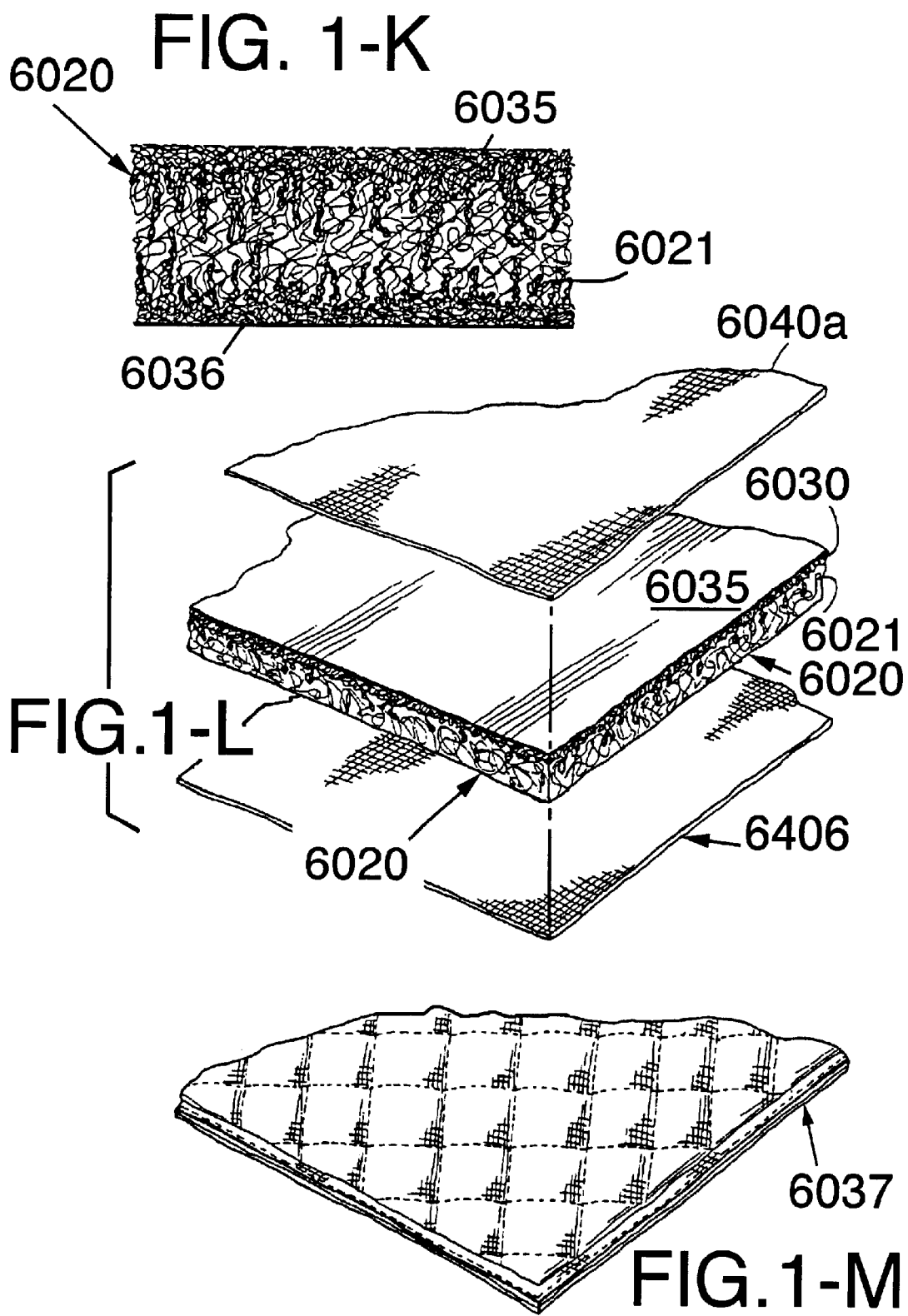

FIG. 6-C

FIG.7-A
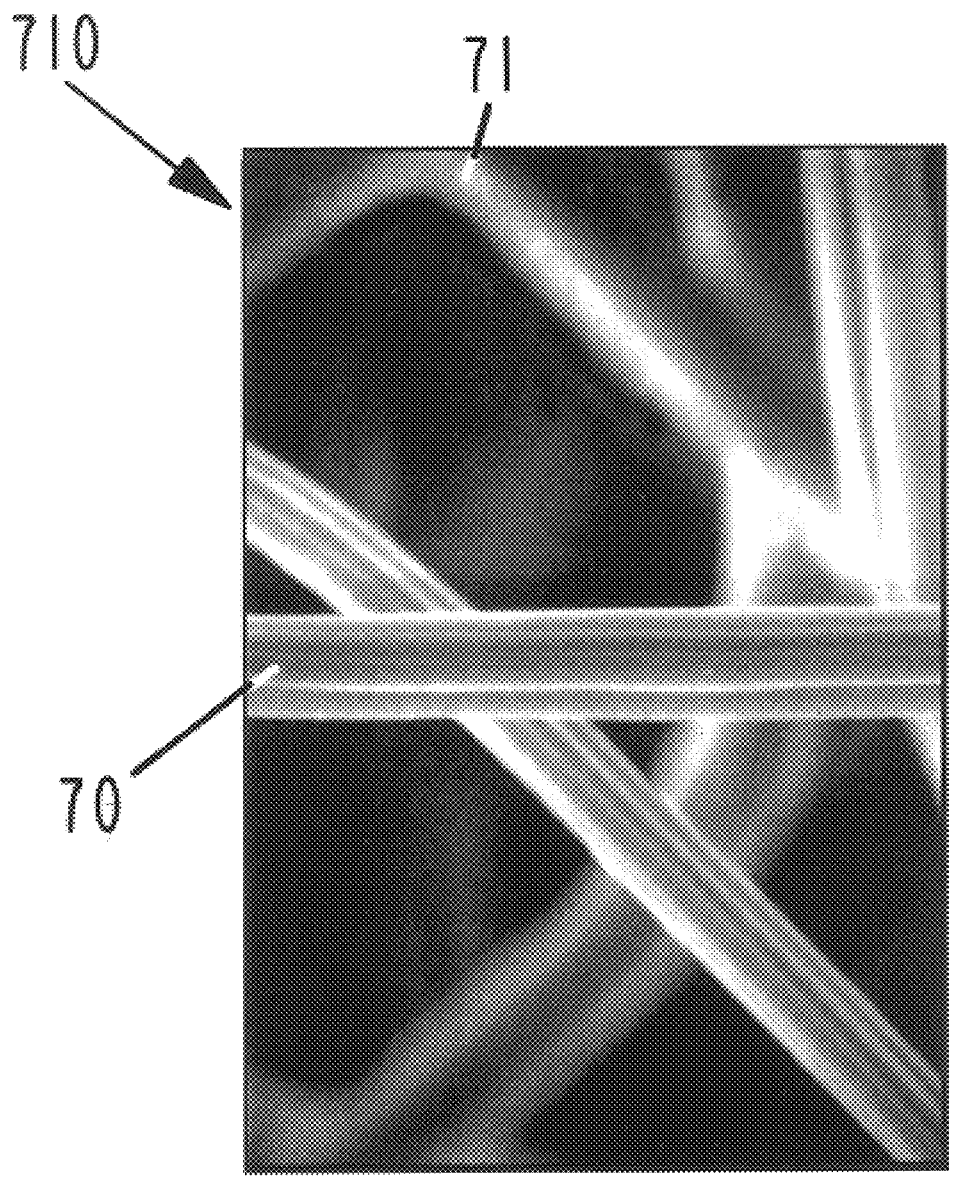

FIG.7-B
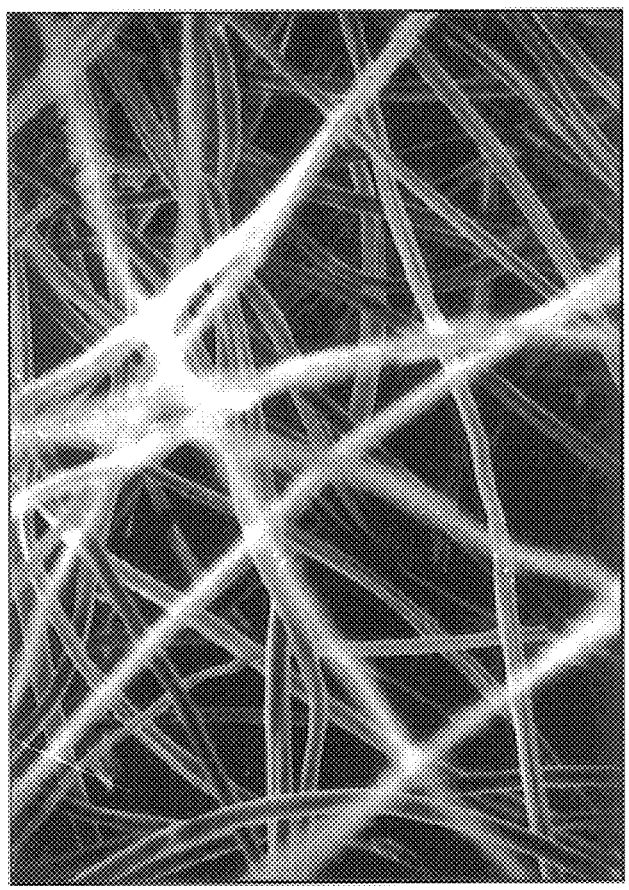

FIG. 7-C
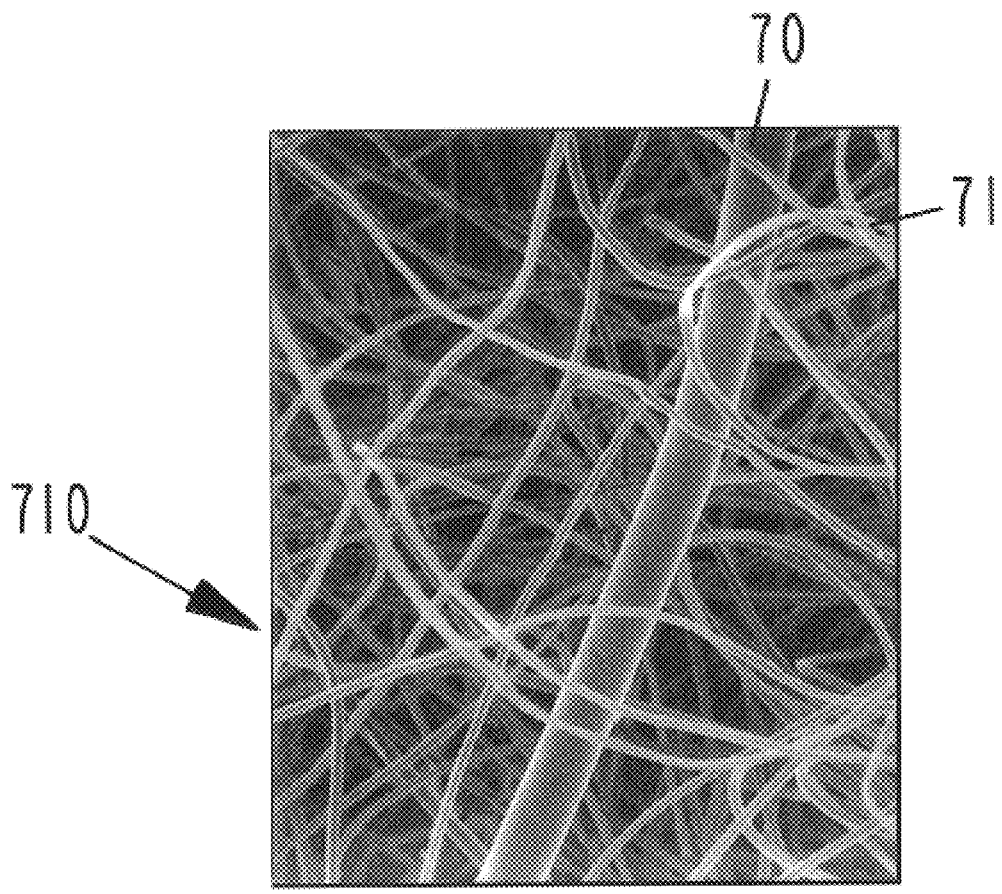

FIG. 7-D
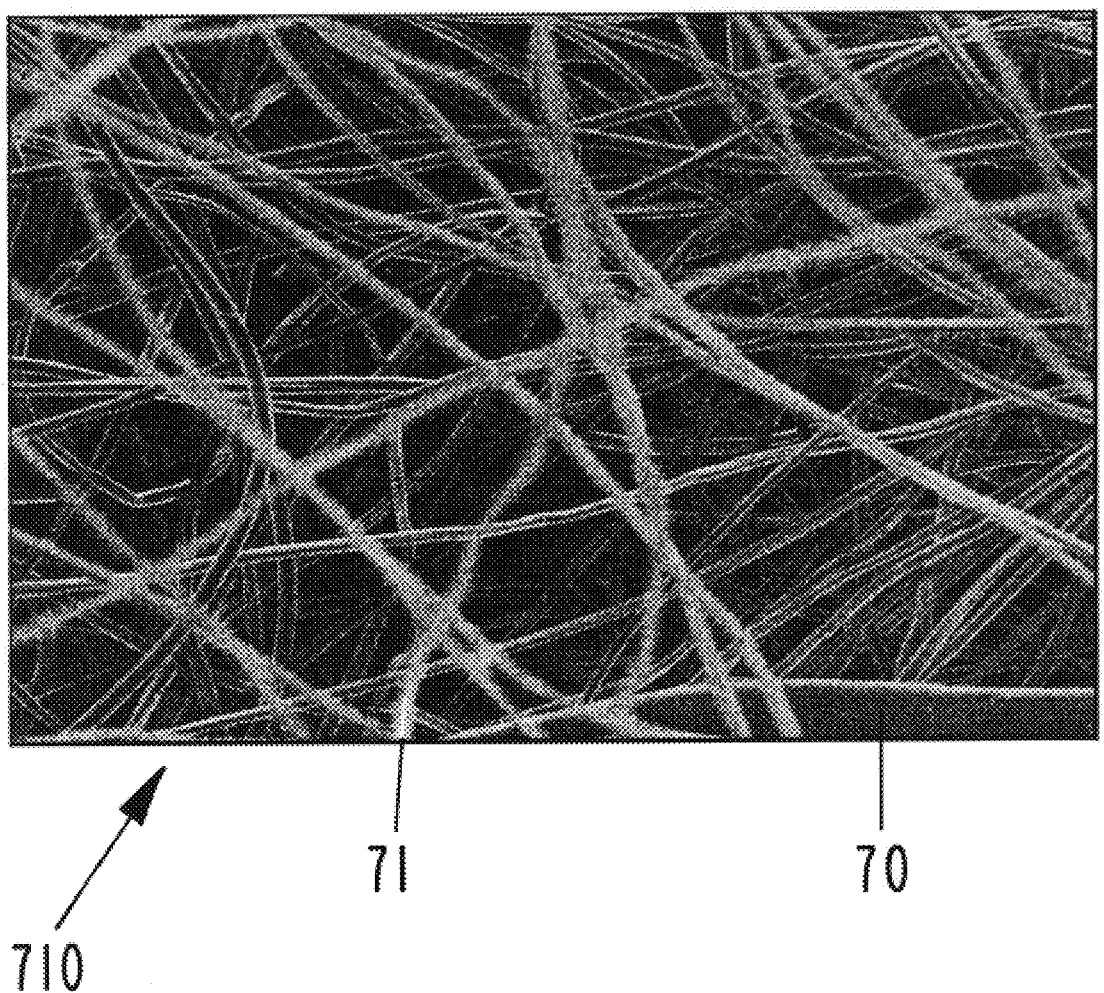

FIG. 7-E
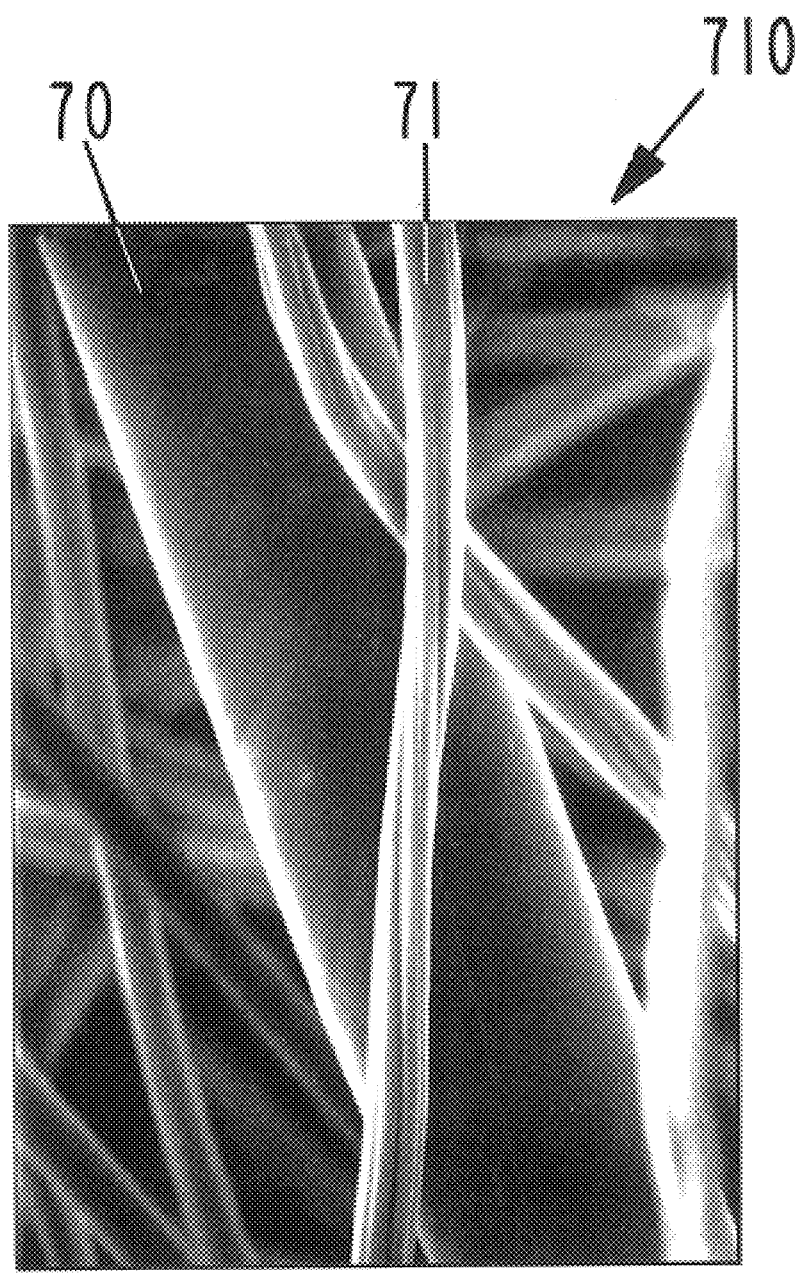

CONTINUOUSLY FRAGRANCE-EMITTING DRY OR WET WIPE FABRIC ARTICLE AND METHOD FOR PREPARING SAME

BACKGROUND OF THE INVENTION

Our invention is directed to a controllably releasable or permanently fragrance-emitting dry or wet wipe laminar fabric article which optionally has efficacious antimicrobial properties comprising a non-woven fabric lamina having woven therethrough and substantially throughout at least a finite portion of the laminar surface, at least one continuous fragrance-imparting component-emitting fiber, which controllably and continuously releases fragrance and, optionally, antimicrobial agent at least for the time period of use of said dry or wet wipe laminar fabric article. Our invention is also directed to a process for the production of such dry or wet wipe laminar fabric article.

Dry and wet wipes are well known commercial consumer products which have been available in many forms. Perhaps the most common form of wet wipes has been a stack of moistened sheets which have been packaged in a plastic container. The wet wipes have been made from a variety of materials which have been moistened with a variety of suitable wiping solutions. Such wet wipes have been used for baby wipes, hand wipes, household cleaning wipes, industrial wipes and the like. By the same token, dry wipes have been made from a variety of materials containing various substances such as antibacterial substances.

With respect to the wet wipes, typically, such conventional wet wipes have included a single layer of a substantially homogeneous material. For example, conventional wet wipes have included an air laid web of fibers which are uniformly mixed or distributed throughout the web. The wipes have included polymeric fibers such as polyester, polyethylene and polypropylene and natural or synthetic fibers such as cellulosic fibers. Other conventional wet wipes have included a co-formed web of polypropylene and cellulosic fibers wherein the fibers are uniformly mixed throughout the web.

European Published Patent Application No. 914,509 published on May 12, 1999 (corresponding to PCT Application No. 98/03713) discloses improved wet wipe articles including a multiple layer base sheet to provide a unique combination of properties to the wipe which are not capable in a single layer base sheet. The layered base sheet includes, in said European Published Patent Application No. 914,509, at least two layers which include different fibers and have different physical properties. One of the layers may include polyethylene fibers to provide a soft, gentle feel for contacting the skin of the user during use while the other layer may include polypropylene fibers to provide strength and resiliency to the wipe to withstand the forces exerted by the user and maintain its shape and integrity in use. The specification of Published European Patent Application No. 914, 509 published on May 12, 1999 as well as the corresponding PCT Application No. 98/03713 and the corresponding United States Application No. 97-U.S.-0723 filed on Jun. 19, 1997 are incorporated herein by reference.

The wet wipes and dry wipes referred to in Published European Patent Application No. 914,509 as well as the corresponding PCT Application No. 98/03713 are not disclosed to be fragranced or fragrancable.

However, fragranced fiber materials are well known in the prior art. Thus, U.S. Pat. No. 3,567,118 issued on Mar. 2, 1971 discloses composite fiber materials which are adapted for odorizing, deodorizing, sanitizing and cleansing purposes by treating the fibrous material with a coating of a hydrophilic acrylate or methacrylate containing an appropriate essence, bactericide, cleansing agent or the like. It is indicated in said U.S. Pat. No. 3,567,118 that both natural and synthetic fibers can be treated with a solution of the hydrophilic polymer, and that entrapment of the chemical agent can be prolonged by using a copolymer of the hydrophilic monomer with a minor amount of a hydrophobic monomer. U.S. Pat. No. 3,567,118 does not set forth the creation of a permanently, continuously fragrancing wet wipe or dry wipe. By the same token, U.S. Pat. No. 3,567,119 issued on Mar. 2, 1971 discloses methods for the incorporating of fragrance compounds or oil bouquets and/or topical antifungal or antibacterial agents, insect repellent compounds and certain odoriferous medicaments into polymeric or natural materials so that the fabricated product possesses the properties imparted by the additive or additives for a long period of time. Further, in U.S. Pat. No. 3,567,119, it is indicated that the efficiency of incorporating additives such as fragrance materials into the articles of the invention is improved by the use of surfactants and the effectiveness and duration of the additive or additives in the fabricated product is enhanced by employing antioxidants and/or ultraviolet radiation absorbers.

However, neither U.S. Pat. No. 3,567,118 nor U.S. Pat. No. 3,567,119 discloses the efficacious continuous and permanent fragrance-emitting dry or wet wipe article of our invention which has woven therethrough fragrance-emitting fiber which is thermoplastic and substantially water-insoluble.

Non-woven fabrics having fibers woven therethrough substantially throughout at least a major portion of the laminar surface thereof are known in the prior art. Thus, U.S. Pat. No. 5,902,757 issued on May 11, 1999 (the specification for which is incorporated herein by reference) discloses a stitch bonded fabric sheet having a felt web with a hydrophobic layer and a hydrophilic layer stitch bonded with yarns to create yarn faces over the respective outer surfaces of the felt web. The sheet may be used as a fluid retention fabric such as to replace the facing fabric and felt layer in an incontinent pad. Nothing is set forth in U.S. Pat. No. 5,902,757 indicating or inferring the utility of such a yarn containing fragrance and/or antimicrobial substance.

However, fragrant fibers per se are well known in the prior art. Thus U.S. Pat. No. 4,713,291 issued on Dec. 15, 1987 discloses fragrant fiber wherein a fragrant sheath-core composite fiber "suitable for bedding" and having a cross section including a sheath and a core including a hollow portion wherein an aromatic perfume having a boiling point higher than 150° C. under normal pressure is incorporated and dispersed in an amount 0.1 to 10.0% by weight in a thermoplastic polymer constituting the core. The core component in U.S. Pat. No. 4,713,291 is preferably a polyethylene-type polymer, and the sheath component is preferably a polyethylene terephthalate polymer. One of the typical compositions of the aromatic perfume of U.S. Pat. No. 4,713,291 is an essential oil mixture including (i) 10 to 20% of lemon oil; (ii) 5 to 15% of bergamot oil; (iii) 2 to 8% of lavender oil; (iv) 2 to 8% of lemongrass oil; (v) 2 to 8% of cedarwood oil and (vi) 0.5 to 1.5% of jasmine absolute. The disclosure of U.S. Pat. No. 4,713,291 is incorporated by reference herein. However, U.S. Pat. No. 4,713,291 does not disclose the use of such fragranced fibers as an essential component of a dry wipe or a wet wipe. Antimicrobial component-containing fibers which can be sewn into textile prostheses for insertion into the body, and epidermal pads and bandages are disclosed in PCT Published Application No. 99/21507 published on May 6, 1999. However, PCT Published Application No. 99/21507 does not disclose the use of such fibers in conjunction with wet wipes or dry wipes and, furthermore, does not disclose the incorporation into such fibers of fragrance materials.

The entire specifications of PCT Published Application No. 99/21507 as well as U.S. Pat. Nos. 3,567,118 and 3,567,119 are incorporated herein by reference.

In summary, although the prior art shows (a) dry wipes and wet wipes made of non-woven fabric; (b) shows fragranced fibers; and (c) shows fragranced non-woven fabrics, nothing in the prior art sets forth wet wipes or dry wipes of our invention which are permanently and continuously fragrance-emitting and, optionally, antimicrobial substance-emitting of our invention.

THE INVENTION

Our invention is directed to a controllably releasable or permanently fragrance-emitting dry or wet wipe laminar fabric article which optionally has efficacious antimicrobial properties comprising a non-woven fabric lamina having woven therethrough and substantially throughout at least a finite portion of the laminar surface at least one continuous fragrance-imparting component-emitting fiber which controllably and continuously releases fragrance and, optionally, antimicrobial agent at least for the time period of use of the dry or wet wipe laminar fabric article.

More specifically, our invention is directed to a permanently and continuously fragrance-emitting dry or wet wipe laminar fabric article comprising a non-woven fabric lamina having woven therethrough and substantially throughout at least a major portion of the lamina surface at least one continuous fragrance-containing thermoplastic substantially water-insoluble fiber which controllably and continuously releases fragrance (which may also have antimicrobial properties) at least for the time period during which the fabric article is in use. Optionally, one or more antimicrobial substances may also be releasably contained in the fiber containing the fragrance or in a fiber apart therefrom. The fabric article optionally contains additional fragrance and/or antimicrobial agent absorbed or adsorbed on the non-woven fabric lamina.

Our invention is also directed to a process for preparing the permanently fragrance-emitting dry or wet wipe laminar fabric article by means of (a) creation of a non-woven fabric lamina optionally containing fragrance which may also have antimicrobial properties and/or at least one antimicrobial agent; (b) creation of the fragrance-containing polymeric fiber which optionally also contains at least antimicrobial agent; and (c) weaving the fragrance-containing fiber through the non-woven fabric lamina substantially across at least a major portion of the surface area of the non-woven fabric lamina.

More specifically, the process of our invention for producing a fragrance-emitting laminar fabric article comprises the sequential steps of:

(a) providing polymer matrix particles having releasably entrapped therein at least one aroma-imparting component which optionally has efficacious antimicrobial properties in a concentration of from about 1% up to about 45% by weight of the polymer particles and, optionally, one or more antimicrobial substances (with the polymer matrix being composed of a thermoplastic substantially water-insoluble polymer);

(b) optionally admixing the matrix particles with a compatible thermoplastic substantially water-insoluble polymer whereby a matrix polymer mixture is formed;

(c) forming the polymer particles or matrix polymer mixture into one or more continuous fragrance-imparting component-emitting fibers of from about 3 denier up to about 60 denier;

(d) providing a non-woven fabric laminar substrate (which may be a monolayer laminar substrate, a bilayer laminar substrate, a trilayer laminar substrate or another multilayer laminar substrate having as much as six layers);

(e) weaving the fragrance-imparting component-emitting fiber or fibers through the non-woven fabric laminar substrate across at least a major portion of the surface area of the non-woven fabric laminar substrate (with the "weaving" operation being, for example, a "needle" punching operation); and (f) optionally adding additional fragrance and/or antimicrobial agent to the resulting laminar fabric article.

The non-woven fabric lamina may be any non-woven fabric lamina known to those skilled in the art, which lamina is substantially water-insoluble, but which has the property of absorbing therein additional water on use of the wet wipe or dry wipe article. Thus, for example, the non-woven fabric may be a filament non-woven fabric comprising thermoplastic conjugated filaments comprising at least one low melting point resin or low softening point resin selected from the group consisting of olefin binary copolymer or olefin terpolymer as the first component and crystalline thermoplastic resin as the second component as set forth in European Published Patent No. 908,549 published on Apr. 14, 1999.

Preferably, the non-woven fabric lamina useful in the practice of our invention contains from about 5 up to about 20% cellulose acetate fiber; from about 10 up to about =30% polypropylene; and from about 50 up to about 80% by weight of viscose.

Furthermore, the non-woven fabric lamina may comprise a non-woven layered base sheet which includes at least two layers positioned in facing relation with each other, 20 at least one of the layers including fibers not included in the other layers as disclosed in Published European Patent Application No. 914,509 published on May 12, 1999, the specification for which is incorporated by reference herein. Thus, European Published Application No. 914,509 claims:

(1) a multilayer of wet wipe comprising:
 (a) a liquid;
 (b) a first non-woven outer layer;
 (c) a second non-woven outer layer positioned in facing position to the first outerlayer; and
 (d) a non-woven inner layer positioned in facing relation between the first outer layer and the second outer layer, with the outer layers including fibers different from those of the inner layer; and (2) a method of providing wet wipes comprising:
 (a) providing a first continuously moving non-woven layer of material;
 (b) providing a second continuously moving non-woven layer of material in facing relation with the first non-woven base sheet, the second layer comprising fibers not included in the first layer;
 (c) a least partially securing the first and second layers together;
 (d) adding a liquid to the layered base sheet; and
 (e) cutting the continuously moving layered base sheet into individual sheets to provide the wet wipes.

Omission of step (d) and consequent omission of the addition of the liquid to the layered base sheet yields a dry wipe sheet as opposed to a wet wipe sheet.

Additional non-woven laminae useful in the practice of our invention are produced according to the processes of U.S. Pat. No. 5,906,890 issued on May 25, 1999, the specification for which is incorporated by reference herein. U.S. Pat. No. 5,906,890 discloses a polypropylene fiber which is suitable for hot rolling and which is used for producing a non-woven fabric having high tenacity and good feel by heat rolling within a wide range of processing temperatures. The polypropylene fiber contains boiling in heptane extract in the amount of 1.5–5% by weight after extraction with boiling in hexane, and the extract has a melting point peak of 140° C. or higher.

The non-woven laminae useful in the practice of our invention can also be produced from olefin polymer fiber containing polypropylene and heterophasic polymer as disclosed in granted European Patent No. 632,148 granted on May 12, 1999, the specification of which is incorporated herein by reference. In said Published European Patent No. 632,148, it is disclosed that an olefin polymer fiber for non-woven fabrics comprises:

(1) 50–80 parts by weight of propylene homopolymer with an isotactic index greater than 90 or a random copolymer of propylene with ethylene and/or $C_4$–$C_8$ α-olefin; and (2) 20–50 parts by weight of heterophasic polymer comprising:
   (a) 20–70 parts by weight of propylene homopolymer and/or a random copolymer of propylene with 0.5–10 weight percent ethylene and/or $C_4$–$C_8$ α-olefin; and
   (b) 30–80 parts by weight of copolymer of ethylene with propylene and/or $C_4$–$C_8$ α-olefin containing 40–47 weight percent ethylene and having a xylene solubility of 45–98% at 25° C. and intrinsic viscosity of no more than 1.5 dl/g or containing less than 40 weight percent ethylene and having an intrinsic viscosity of no more than 2.3 dl/g; the fiber being obtained by spinning via an orifice with an actual or equivalent diameter of less than 0.5 mm and then drawing at a ratio of 1.1 up to 1.8.

The polymer matrix particles having releasably entrapped therein at least one aroma-imparting component which optionally has efficacious antimicrobial properties may be prepared according to processes well known in the prior art, for example, the processes as set forth in U.S. Pat. No. 4,542,162 issued on Sep. 17, 1985, the specification for which is incorporated herein by reference. Furthermore, such polymer matrix particles having releasably entrapped therein at least one aroma-imparting component may also be prepared according to United Kingdom Patent Specification No. 1,589,201 assigned to Hercules, Inc., which discloses a thermoplastic resin body consisting of a thermoplastic polymer of ethylene and 6–60 weight percent of a polar vinyl monomer selected from the group consisting of vinyl acetate, methyl acrylate, ethyl acrylate, buytl acrylate and acrylic acid wherein the perfumed resin body is suitable for the preparation of shaped objects from which the perfume odor emanates over a prolonged period at a stable level. Another process for preparing the polymer matrix particles having releasably entrapped therein at least one aroma-imparting component is U.S. Pat. No. 3,505,432, the specification for which is incorporated by reference herein. U.S. Pat. No. 3,505,432 discloses a method of scenting a polyolefin and forming polyolefin-scented particles which comprises:

(a) mixing a first amount of liquid polyolefin, e.g., polyethylene or polypropylene, with a relatively large amount of scent-imparting material to form a flowable mass;

(b) forming drops from said mass and causing substantially instantaneous solidification of said drops into polyolefin pellets having a relatively large amount of scent-imparting material imprisoned therein;

(c) if desired, melting said pellets with a second amount of said polyolefin, said second amount being larger than said first amount; and (d) solidifying the melt of (c).

Other references which disclose microporous polymers useful in the practice of our invention are set forth as follows:

(a) U.S. Pat. No. 4,247,498 issued on Jan. 27, 1981, the specification for which is incorporated by reference herein;

(b) U.S. Pat. No. 4,156,067 issued on May 22, 1979, the specification for which is incorporated by reference herein; and (c) U.S. Pat. No. 4,521,541 issued on Jun. 4, 1985, the specification for which is incorporated by reference herein.

The resulting polymer matrix particles having releasably entrapped therein at least one aroma-imparting component, may then be further admixed with additional compatible polymer. Thus, for example, additional polypropylene may be admixed with polypropylene particles which contain between about 1 and about 45% by weight of the polymer of fragrance.

The resulting mixture or the resulting polymer matrix particles having releasably entrapped therein at least one aroma-imparting component is then formulated into one or more continuous fragrance-imparting component-emitting fibers of from about 3 denier up to about 60 denier (1 denier means that 9,000 meters of fiber weigh 1 gram). The resulting mixtures can be formulated into such fibers by means of specific extruders for fiber manufacturing produced, for example, by the Davis-Standard Corporation of #1 Extrusion Drive, Pawcatuck, Conn. 06379. Such extrusion apparatus is preferably equipped with "hot runner" systems which enable the fibers to be produced at a uniformly constant diameter and to be produced in large quantity in an efficient manner.

In producing the fiber for purposes of weaving same into the lamina surface, it is preferred that the weight ratio of the polymer matrix particles having releasably entrapped therein at least one aroma-imparting component: additional compatible polymer being from about 2:1 down to about 1:1 with a preferred weight ratio of matrix particle:additional polymer being about 1.5:1.

The fibers of our invention which are used for weaving through the lamina surface need not necessarily be produced from matrix particles as set forth, supra. Instead, fragrance-emitting fibers for use in weaving same through the lamina surface of non-woven fabric may be produced according to processes as set forth in:

(a) PCT Application No. 99/21507 published on May 6, 1999;

(b) U.S. Pat. No. 4,713,291 issued on Dec. 15, 1987; and (c) U.S. Pat. No. 3,567,118 issued on Mar. 2, 1971.

Each of the foregoing documents are incorporated herein by reference.

In PCT Application No. 99/21507, there is disclosed a synthetic fiber having cavities for holding large quantities of active material exemplified by medicaments. The Fragrance materials can be introduced into such fibers in place of the disclosed medicaments. Thus, alternative processes for producing such fibers are as follows:

(i) manufacturing fibers by extruding a plural-component fiber from a spinneret, dissolving a soluble component to form cavities and securing a fragrance into the cavities;

(ii) manufacturing fibers by extruding a single component fiber from a spinneret forming cavities and introducing therein fragrance components; and (iii) manufacturing fibers by mixing a fragrance with a polymer and extruding the resulting mixture from a spinneret and forming island-in-the-sea plural-component fibers.

In U.S. Pat. No. 4,713,291, a fragrant sheath core composite fiber having a cross section including a sheath and a core including a hollow portion is produced wherein an aromatic perfume having a boiling point higher than 150° C. under normal pressure is incorporated and dispersed in an amount of from about 0.1 up to about 10.0% by weight in a thermoplastic polymer constituting the core. The core component is preferably a polyethylene-type polymer and the sheath component is preferably a polyethylene terephthalate polymer.

In U.S. Pat. No. 3,567,118, composite fiber materials are adapted for odorizing purposes by treating the fibrous material with a coating of a hydrophilic acrylate or methacrylate containing an appropriate essence. Entrapment of the essence can be prolonged by using a copolymer of the hydrophilic monomer with a minor amount of a hydrophobic monomer.

Fragrance materials which are preferably incorporated in the polymer matrix particles or which are, in general, incorporated into the fiber, which is to be woven through the lamina surface, are preferably those fragrances which also have antimicrobial properties; for example, those set forth in Published Japanese Application No. JP101/94905 assigned to the Lion Corporation and published on Jul. 28, 1998, to wit:

(a) one or more aldehydes selected from cinnamic aldehyde, benzaldehyde, phenyl acetaldehyde, heptylaldehyde, octylaldehyde, decylaldehyde, undecylaldehyde, undecylenic aldehyde, dodecylaldehyde, tridecylaldehyde, methylnonyl aldehyde, didecylaldehyde, anisaldehyde, citronellal, citronellyloxyaldehyde, cyclamen aldehyde, α-hexyl cinnamic aldehyde, hydroxycitronellal, α-methyl cinnamic aldehyde, methylnonyl acetaldehyde, propylphenyl aldehyde, citral, perilla aldehyde, tolylaldehyde, tolylacetaldehyde, cuminaldehyde, LILIAL®, salicyl aldehyde, α-amylcinnamic aldehyde and heliotropin; and (b) from about 0.01 up to about 10 weight percent of one or more crystallization controlling agents selected from dibutyl hydroxytoluene, butyl hdroxyl amisole, propyl gallate, α-tocopherol, isopropyl citrate, erysorbic acid, sodium erysorbate, guaiac resin, calcium disodium ethylenediamine tetra acetate and disodium ethylenediamine tetra acetate.

Other preferable fragrance compositions are those set forth in U.S. Pat. No. 5,420,104 issued on May 30, 1995, the specification for which is incorporated by reference herein. Such perfume compositions as described in U.S. Pat. No. 5,420,104 contain a cationic phospholipid having the structure:

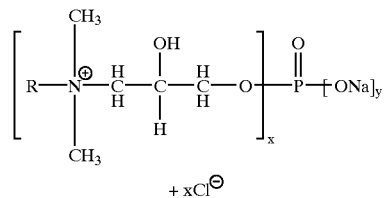

wherein R is linoleamidopropyl or cocamidopropyl; and X+y=3; a perfume base having antimicrobial activity and a fatty alcohol having from 10 up to 22 carbon atoms. Such a perfume base having antimicrobial activity contains:

benzyl acetate;

cyclohexyl acetate styrallyl acetate;

n-octanol;

n-decanol;

amylcinnamic aldehyde rosewood oil;

geraniol;

clove oil;

methyl jasmonate;

hydroxycitronellal;

methyl dihydrojasmonate;

ylang oil; and mixture of methylionone isomers.

Furthermore, perfume compositions such as those set forth in:

U.S. Pat. No. 5,300,489 issued on Apr. 5, 1994 (the specification for which is incorporated by reference herein);

U.S. Pat. No. 5,932,771 issued on Aug. 3, 1999 (the specification for which is incorporated by reference herein); or U.S. Pat. No. 5,942,272 issued on Aug. 24, 1999 (the specification for which is incorporated by reference herein), may also be utilized in the fragrance-containing fiber which controllably and continually releases fragrance and which is woven through the major portion of the laminasurface of the non-woven fabric.

Thus, for example, the fragrance formulation contained in the fragrance-containing fiber which controllably and continuously releases fragrance, may include:

dihydromethyl jasmonic acid;

geraniol;

citronellol; and oil of chamomile.

Along with the fragrances contained in the fragrance-containing fiber which controllably and continuously releases fragrances, the fiber may optionally have incorporated therein antimicrobial agents such as those set forth in the following list:

triclosan having the structure:

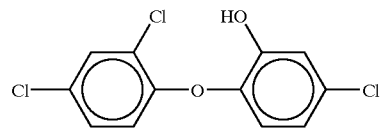

(an example is IRGASAN® DP 300, a trademark of Ciba Specialty Chemicals Holding Incorporated of Basel, Switzerland);

triclocarban having the structure:

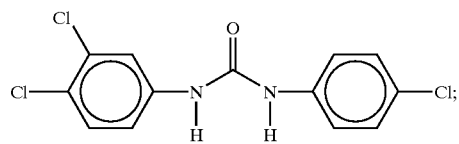

the compound having the structure:

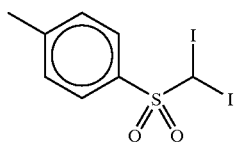

marketed as AMICAL® by Angus Chemie GmbH of Zeppelinstrasse, Ibbenbuhren, Germany;

the compound having the structure:

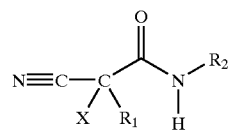

where X is halogen; $R_1$ is hydrogen, halogen or alkyl; $R_2$ is hydrogen or alkyl; and $R_3$ and $R_4$ are the same or different hydrogen, halogen or alkyl;

the compound having the structure:

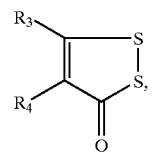

a 2,3-dithiolane wherein $R_3$ and $R_4$ are the same or different hydrogen, alogen or alkyl, for example, the compound having the structure:

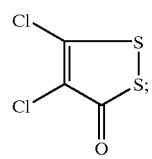

the compound having the structure:

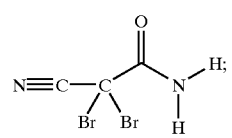

the compound having the structure:

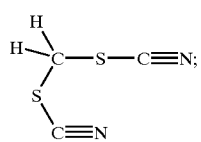

a compound having the structure:

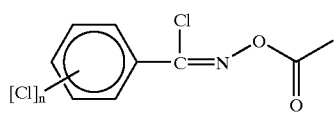

wherein n is 0, 1 or 2;

the compound having the structure:

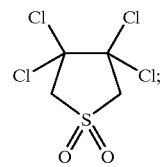

the compound having the structure:

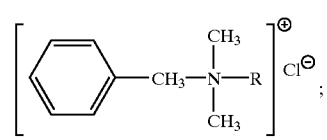

the compound having the structure:

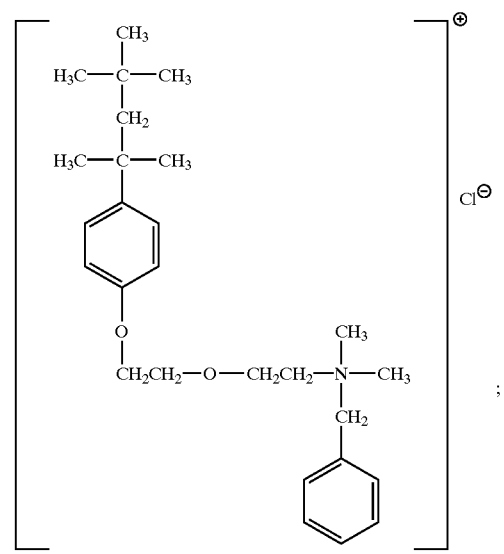

the compound having the structure:

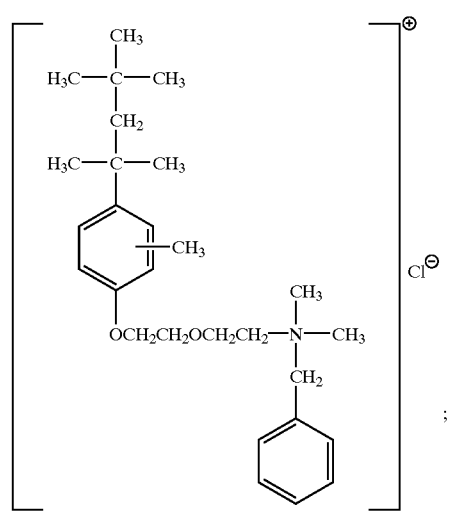

the compound having the structure:

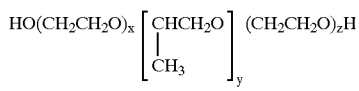

wherein the average values of x, y and z are, respectively, 75, 30 and 75;

compounds defined according to the structure:

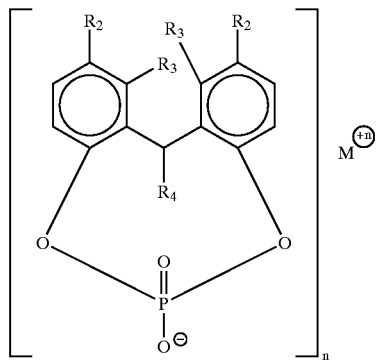

wherein n is 1 or 2 and M is alkali metal when n is 1 or alkaline earth metal when n is 2; wherein $R_4$ is hydrogen or methyl and $R_2$ and $R_3$ are hydrogen or $C_{1-C18}$ alkyl as exemplified in Japanese Published Application JP111/16822, incorporated herein by reference; and compounds defined according to the structure:

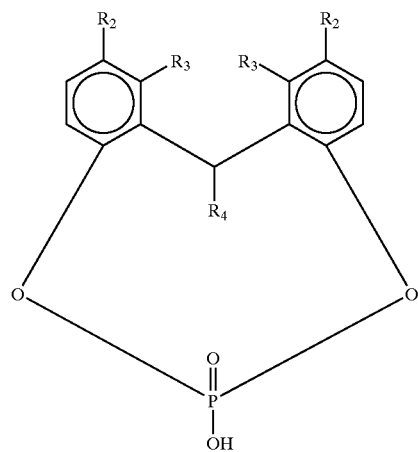

wherein $R_2$ and $R_3$ represent hydrogen, or $C_1$–$C_{18}$ alkyl and $R_4$ is hydrogen or methyl (as exemplified in Japanese Published Application No. JP111/16822, incorporated herein by reference).

In addition to the fragrance ingredients together with the optional antimicrobial agents being present in the fiber used to be woven through the lamina of the non-woven fabric article of our invention, fragrance and/or antimicrobial agent as described, supra, may also be incorporated into the non-woven fabric itself, in addition to such fragrance being incorporated into the fiber. The presence of fragrance in the non-woven fabric article permits an initial "burst" of fragrance on use of the dry wipe or wet wipe and, in addition, the continuous controlled release of fragrance on continued use of the dry wipe or wet wipe article. In addition, the antimicrobial agent when incorporated directly into the non-woven lamina article provides an initial "burst" of antimicrobial agent in addition to continuous release of antimicrobial agent when such agent is incorporated into the continuous fragrance-containing fiber which controllably and continuously releases fragrance at least for the period of time during which the fabric article is in use.

The step of weaving the fragrance-imparting component-emitting fiber or fibers (once they are produced) through the non-woven fabric laminar substrate across at least a major portion of the surface area of the non-woven fabric laminar substrate is carried out by means of "stitch bonding" as more specifically described in such references as U.S. Pat. No. 5,902,757 issued on May 11, 1999, the specification for which is incorporated herein by reference. Thus, referring to U.S. Pat. No. 5,902,757, a stitch bonded fabric sheet has a felt web with a hydrophobic layer and a hydrophilic layer stitch bonded with yarns to create yarn faces over the respective outer surfaces of the felt web. The bonded fabric sheet may be used as a fluid retention fabric such as to replace facing fabric and a felt layer in a wet wipe or dry wipe article. Thus, the "yarn" of U.S. Pat. No. 5,902,757 is replaced in accordance with our invention with a continuous fragrance-containing fiber which controllably and continuously releases fragrance at least for the time period during which the fabric article is in use. As stated, supra, such continuous fragrance-containing fiber also may contain antimicrobial agent.

The quantity of fragrance material in the fragrance-containing fiber may vary from about 1% up to about 45% by weight of fragrance when no antimicrobial agent is present; or the sum total of antimicrobial agent and fragrance may vary from about 1% up to about 45% by weight of the fiber when antimicrobial agent is present. Preferably, the amount of fragrance or sum total of fragrance and antimicrobial agent varies between about 1% and about 20% by weight of the fiber.

Optionally, the additional fragrance and/or antimicrobial agent can be added to the laminar fabric article prior to weaving the fragrance-imparting component-emitting fiber or fibers through the non-woven fabric laminar substrate or subsequent to weaving the fragrance-imparting component-emitting fiber or fibers through the non-woven fabric laminar substrate or both prior to and subsequent to weaving the fragrance-imparting component-emitting fiber or fibers through the non-woven fabric laminar substrate.

Thus, in summary, the process for producing a fragrance-emitting laminar fabric article of our invention comprises more broadly the sequential steps of:

(a) forming one or more continuous fragrance-imparting component-emitting fibers optionally containing antimicrobial agent, of from about 3 denier up to about 60 denier;

(b) providing a non-woven fabric laminar substrate;

(c) weaving said fragrance-imparting component-emitting fiber or fibers through said non-woven fabric laminar substrate across at least a major portion of the surface area of the non-woven fabric laminar substrate; and (d) optionally adding additional fragrance and/or antimicrobial agent to the resulting laminar fabric article.

Alternatively, the process of our invention comprises the sequential steps of:

(a) providing a non-woven fabric laminar substrate;

(b) optionally adding fragrance and/or antimicrobial agent to the fabric laminar substrate;

(c) forming one or more continuous fragrance-imparting component-emitting fibers optionally containing antimicrobial agent of about 3 denier up to about 60 denier; and (d) weaving said fragrance-imparting component-emitting fiber or fibers through said non-woven fabric laminar substrate across at least a major portion of the surface area of the non-woven fabric laminar substrate.

Alternatively, the process of our invention comprises the sequential steps, broadly, of:

(a) providing a non-woven fabric laminar substrate;

(b) optionally adding fragrance and/or antimicrobial agent to the non-woven fabric laminar substrate;

(c) forming one or more continuous fragrance-imparting component-emitting fibers optionally containing antimicrobial agent of about 3 denier up to about 50 denier;

(d) weaving said fragrance-imparting component-emitting fiber or fibers through said non-woven fabric laminar substrate across at least a major portion of the surface area of the non-woven fabric laminar substrate; and (e) optionally adding additional fragrance and/or additional antimicrobial agent to the resulting laminar fabric article.

Additional non-woven fabrics which may be used in the practice of our invention are referred to in the following references:

PCT Application No. 99/19452 published on Apr. 22, 1999 ("laundry treatment products for SPANDEX®-containing fabrics), incorporated by reference herein (PCT Application 99/19452 discloses a fabric treatment product containing a perfume which includes a mixture of fragrance materials for the treatment of garments containing SPANDEX® and other fibers, preferably after wearing thereof, to deposit fragrance materials to a greater extent on the SPANDEX® fibers other than on the other fibers);

U.S. Pat. No. 5,454,142 issued on Oct. 3, 1995 ("NONWOVEN FABRIC HAVING ELASTOMETRIC AND FOAM-LIKE COMPRESSIBILITY AND RESILIENCE AND PROCESS THEREFOR"). In U.S. Pat. No. 5,454,142, a needlepunch fabric of staple polyester fibers is disclosed that is elastomeric and has foam-like compressibility and resilience. The polyester staple is formed of fibers having a differential berefringence. Mechanically crimped fibers are carded, cross-lapped and needlepunched to from about 150 to 1,500 ppsi, and the resultant fabric is heated to from about 120° C. up to about 240° C. to induce a latent crimp in the fabric and to develop the elastomeric and foam-like properties of the fabric. U.S. Pat. No. 5,454,142 issued on Oct. 3, 1995 is incorporated herein by reference;

U.S. Pat. No. 5,906,890 issued on May 25, 1999, the specification for which is incorporated by reference herein;

U.S. Pat. No. 5,881,440 issued on Mar. 16, 1999, the specification for which is incorporated by reference herein;

U.S. Pat. No. 5,824,610 issued on Oct. 20, 1998, the specification for which is incorporated by reference herein. U.S. Pat. No. 5,824,610 discloses a non-woven fabric of chemically bonded non-cellulose fibers having improved wet tensile properties. The fabric includes a random arrangement of non-cellulose fibers and an essentially formaldehyde-free latex binder. The latex binder contains at least 6.7 weight percent vinyl cyanide monomer to bond the non-cellulose fibers and form a non-woven fabric having at least 10% improvement in wet tensile strength over a comparable non-woven fabric having latex binder essentially of formaldehyde and free of vinyl cyanide monomer in the monomeric mixture;

PCT Application No. 99/22619 published on May 14, 1999, the specification for which is incorporated by reference herein;

PCT Application No. 99/22059 published on May 6, 1999, the specification for which is incorporated by reference herein;

U.S. Pat. No. 5,783,503 issued on Jul. 21, 1998, the specification for which is incorporated by reference herein. In U.S. Pat. No. 5,783,503, it is disclosed that multicomponent thermoplastic continuous filaments are provided, including hollow core multicomponent filaments. The filaments are at least partially splitable into smaller filaments in the absence of mechanical treatment or application of high pressure water jets. The surface energy of the components can be controlled to control separation of the multicomponents' filaments. Subdenier and microdenier filaments of low orientation can be produced in U.S. Pat. No. 5,783,503 from relatively high molecular weight polymers to produce non-woven fabrics of relatively high strength, barrier and cover;

U.S. Pat. No. 5,631,083 issued on May 20, 1997, the specification for which is incorporated by reference herein. U.S. Pat. No. 5,631,083 discloses a drawn, polyolefin fiber useful for non-woven fabrics with a thermobonding index being from about 4.5 up to about 9 Newtons and a flexibility being from 1,020 up to 1,500. The fiber of U.S. Pat. No. 5,631,083 is composed of a blend of specific polymers. Also disclosed in U.S. Pat. No. 5,631,083 is a process for making the fiber by spinning the blend from a die hole having at the output end a diameter less than 0.5 mm and drawing the resulting fiber at a draw ratio of 1:1 to 1:8; and U.S. Pat. No. 5,925,581 issued on Jul. 20, 1999, the specification for which is incorporated by reference herein. U.S. Pat. No. 5,925,581 discloses a textile laminate comprising a fiber fill web substrate and a face layer. The fiber fill web substrate has a plurality of first fibers at the surface of the substrate. The face layer comprises a plurality of extruded second fibers which are mechanically intertangled with the plurality of first fibers at the surface of the substrate to thereby form the textile laminate. The first fibers of the fiber fill web of U.S. Pat. No. 5,925,581 are polyester fiber fill fibers and the second fibers of the extruded face layer are polypropylene fibers. The non-woven fabrics of U.S. Pat. No. 5,925,581 incorporated by reference herein are particularly suitable for use in conjunction with our invention.

Also useful in the practice of our invention are the antimicrobial mixtures claimed in the following patents and published patent applications:

Japan Published Application No. 28/91622 granted on May 17, 1999 discloses and claims antibacterial agents which are mixtures of the compounds having the structures:

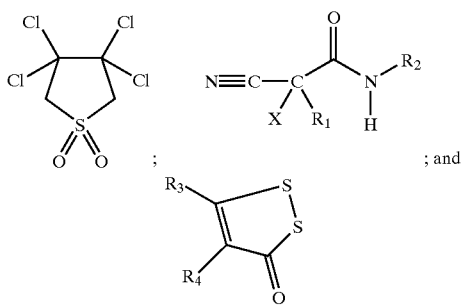

; and wherein X is halogen; $R_1$ is hydrogen, halogen or alkyl; $R_2$ is hydrogen or alkyl; and $R_3$ and $R_4$ are the same or different hydrogen, halogen or alkyl;

Japan Published Application No. 28/91623 granted on May 17, 1999 discloses and claims a mixture of compounds having the structures:

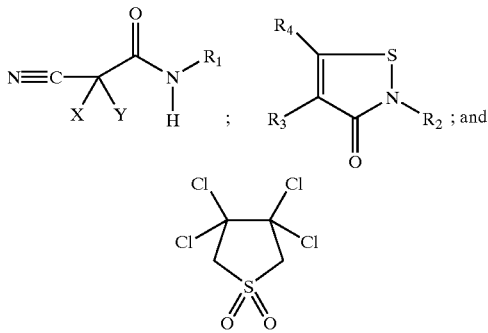

wherein X is halogen; Y is hydrogen or halogen; $R_1$ is hydrogen or lower alkyl; $R_2$ is hydrogen or hydrocarbyl; and $R_3$ and $R_4$ are the same or different hydrogen or halogen;

Japan Published Application No. 28/91629 granted on May 17, 1999 discloses the use as an antimicrobial mixture of the compounds having the structures:

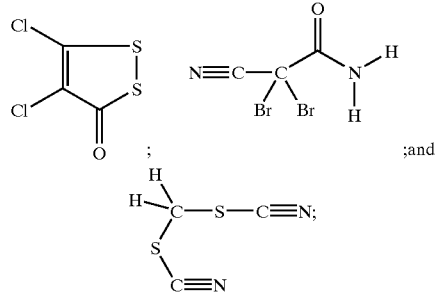

Japan Published Application No. 28/91635 granted on May 17, 1999 discloses the use as an antimicrobial mixture of the mixture of compounds having the structures:

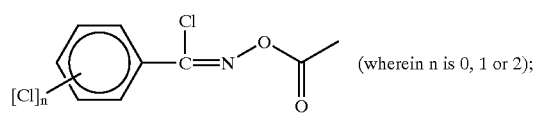
(wherein n is 0, 1 or 2);

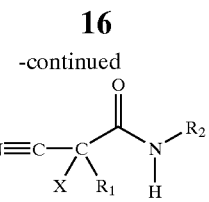

(wherein X is halogen; $R_1$ is hydrogen, halogen or alkyl; $R_2$ is hydrogen or alkyl; and $R_3$ and $R_4$ are the same or different hydrogen, halogen or alkyl); and the compound having the structure:

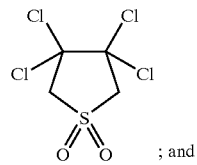
; and

European Published Application No. 917880 published on May 26, 1999 discloses an inclusion complex of the compound having the structure:

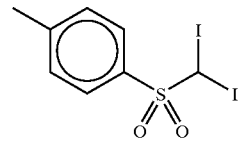

with cyclodextrin derivatives.

Other polymers that can be used for creation of the continuous fragrance-containing fiber which controllably and continually releases fragrance at least for the time period during which the fabric article is in use are disclosed in PCT Application No. US 99-05657 (PCT Serial No. 97 93 86 14.1, the disclosure of which is incorporated by reference herein). PCT Application No. US 99-05657 discloses the fragrance-emitting specially designed hydrophilic polyurethanes with certain hydrophobic components that retain aroma chemicals in the dry state and provide sustained fragrance release upon moisture exposure. The polymers are soluble in solvent mixtures ranging from 95:5 up to 20:80 weight:weight propylene glycol:water. In addition, they are also soluble in solvent mixtures of lower alcohols:water with similar ranges. Accordingly, the wet wipes and dry wipes which are composed of the polymers of PCT Application No. US 99-05657 are not to be used within the scope of this invention with alcohol or propylene glycol.

Additional perfumed fibers and antimicrobial product-containing fibers which can be employed in the practice of our invention are set forth in the following references (incorporated by reference herein):

Japan Published Application No. 63/135573 published on Jun. 7, 1988 (perfumed fiber production by applying perfume emulsifier including spinning oil to fiber and heating in steam), assigned to Takasago Perfumery Company, Ltd.; and Japan Published Application No. 111/17174 published on May 27, 1999 discloses an antimicrobial fiber made up of polyester resin having a surface layer containing an antimicrobial agent. The antimicrobial agent consists of a quaternary phosphonium salt group which bonds ionically with an acid component of a hydrophilic resin (assigned to Toyobo KK).

In formulating polymer matrix particles having releasably entrapped fragrances or fragrance components therein and optionally one or more antimicrobial substances entrapped therein, the procedure of U.S. Pat. No. 4,542,162 granted on Sep. 17, 1985 may be utilized thusly:

foamed fragrance-containing polymeric pellets are produced by means of introduction into a single screw or twin screw extruder of, in series, thermoplastic polymer followed by fragrance followed by the introduction of a gaseous blowing agent or blowing agent which will produce a gas which is inert to the polymer and to the fragrance fluid or solid previously introduced into the extruder. Antimicrobial agent optionally may be introduced simultaneously with the introduction of fragrance or upstream from the point of introduction of fragrance into the extruder or downstream from the point of introduction of the fragrance into the extruder.

The advantages of using the foamed polymeric particles are multiple, to wit: improved handling; greater retention of fragrance; and, if desired, antimicrobial agent; greater length of time during which release of fragrance and, optionally, antimicrobial agent from polymer is at "steady state" or "zero order."

The nature of the extruder utilized in the process of our invention to form the foamed polymeric fragrance-containing polymer particles of our invention may be either single screw or double screw. Thus, the types of extruders that can be used are disclosed at pages 246–267 and 332–349 of the *Modern Plastics Encyclopedia*, 1982–1983, published by the McGraw-Hill Publishing Company, the disclosure of which is incorporated by reference herein. Similarly, such extruders are disclosed in the *Modern Plastics Mid-November* 1996 *Encylcopedia*, published by the McGraw-Hill Publishing Company, the disclosure of which is incorporated by reference herein. More specifically, examples of extruders which are usable in carrying out this aspect of the process of our invention are as follows:

1. The Welex "Super Twinch" 3.5 inch extruder manufactured by Welex Incorporated, 850 Jolly Road, Blue Bell Pa. 19422;
2. Krauss-Maffei twin screw extruder manufactured by the Krauss-Maffei Corporation/Extruder Division, 3629 West 30th Street South, Wichita, Kan. 67277;
3. Modified Sterling model 4000 and 5000 series extruder manufactured by Sterling Extruder Corporation of 901 Durham Avenue, South Plainfield, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder maufactured by the Werner & Pfleiderer Corporation of 663 East Crescent Avenue, Ramsey, N.J. 07746;
7. The Farrel Extruder manufactured by Farrel Connecticut Division, Emhart Machinery Group, Ansonia, Conn. 06401;
8. The MPCNV Baker Perkins Twin Screw Extruder manufactured by the Baker Perkins Inc. Chemical Machinery Division of Saginaw, Mich. 48601; and
9. The Berstorff single screw, twin screw or foam extrusion equipment manufactured by the Berstorff Corporation, P.O. Box 240357, 8200-A Arrowridge Boulevard, Charlotte, N.C. 28224.

In producing the foamed fragrance-containing polymer particles of our invention (which optionally contain antimicrobial agent), various polymers may be utilized, for example, low density polyethylene, high density polyethylene, polypropylene, the copolymer of ethylene and vinyl acetate, and polyvinyl chloride. More specifically, the polymers used in the practice of our invention may be copolymers of ethylene and a polar vinyl monomer selected from:

(a) vinyl acetate;
(b) ethyl acrylate;
(c) methyl acrylate;
(d) butyl acrylate; and
(e) acrylic acid, including the hydrolyzed copolymer of ethylene and vinyl acetate. Preferred co polymers are ethylene vinyl acetate with about 9 to 60% vinyl acetate and ethylene/ethyl acrylate with about 6 to 18% ethyl acrylate. As set forth, supra, other polymers which may be admixed with such materials include the polyurethane polymers of PCT Application No. PCT-US99-05657, incorporated herein by reference.

Resins of the type disclosed for use as copolymers are commercially available in the molding powder form. For example, ethylene vinyl acetate copolymers are marketed by the E.I. duPont de Nemours Company under the tradename "ELVAX" and by the Arco Polymer Division under the trademark "DYLAND®" and by the Exxon Corporation of Linden, N.J. under the trademark "DEXXON®." Ethylene/ethyl acrylate copolymers are marketed by the Union Carbide Corporation under the tradename "EEA RESIN®."

The polymer is added to the single screw or twin screw extruder at a feed rate in the range of from about 80 up to about 300 lbs per hour, while maintaining the temperature in the screw extruder between about 160 and about 240° C. If the polymer or copolymer powder is added to the extruder at a reference "barrel segment," then the fragrance and, optionally, the antimicrobial agent is added to the extruder in solid or liquid form under pressure downstream from the addition point of the polymer at one or more "barrel segments" 2–9.

Thus, this aspect of our invention provides a process for forming fragrance and, optionally, antimicrobial liquid or solid-containing foamed polymeric particles such as foamed polymeric pellets, which include a relatively high concentration of a material having at least the function of fragrancing and, optionally, the function of imparting antimicrobial properties to the ultimately-produced fiber. The fragrance and, optionally, the antimicrobial agent in a fluid or solid form are added at "barrel segments" 2–9 of the single screw or twin screw extruder. Furthermore, the fragrance and optionally antimicrobial agent added at "barrel segments" 2–9 must be previously made to be compatible with the polymer added at "barrel segment" 1 of the single screw or twin screw extruder.

The use as to type and proportion of fragrance and optionally antimicrobial agent is limited only by either (a) their solubility in the resin or mixture of resins used and/or (b) the volume ratio of microvoids in the polymer to the said polymer and/or (c) the solubility of the fragrance and optionally antimicrobial agent in the polymer on solidification. The proportion of fragrance and optionally antimicrobial agent can in many instances go up to 45% by weight based on the total weight of fiber which is to ultimately be used in being woven across at least a major portion of the surface area of the non-woven fabric laminar substrate.

Thus, the proportion of fragrance and optionally antimicrobial agent to the weight of resin body for formation of the fiber to be woven across the non-woven fabric lamina can vary from small but effective amounts on the order of about 1% of the weight of the resin body (that makes up the fiber) up to about 45% by weight of the resin body (that makes up the weight of the fiber). In general, it is preferred to use between about 1% up to about 30% based on the weight of the resin body of the fragrance taken alone or taken together with optional antimicrobial agent. This is an optimum amount balancing the proportion of fragrance and optionally antimicrobial agent in the product against the time period over which the article emits the fragrance and optionally the antimicrobial agent, and against the tendency of the fragrance and optionally antimicrobial agent fluid or solid to oil out." This "oiling out" is avoided as a result of the use of foaming agent.

BRIEF DESCRIPTION OF THE DRAWINGS

FIG. 1A is a schematic block flow diagram of a specific embodiment of the process of our invention showing the use of polymer matrix particles having releasably entrapped therein at least one aroma-imparting component.

FIG. 1B is another schematic block flow diagram showing another embodiment of a process of our invention wherein polymer matrix particles having releasably entrapped aroma-imparting components are utilized.

FIG. 1C is also a block flow diagram of another embodiment of the process of our invention showing the use of polymer matrix particles having releasably entrapped therein at least one aroma-imparting component.

FIG. 1D is another block flow diagram of an embodiment of the process of our invention showing the use of polymer matrix particles having releasably entrapped therein at least one aroma-imparting component.

FIG. 1E is a schematic side elevation view of apparatus which carries out a process for production of non-woven fabric useful in the practice of our invention.

FIG. 1F is a diagrammatic partially broken away, cross sectional view of a sheet of stitch bonded non-woven fabric produced in accordance with the principles of the present invention wherein the bonding "yarn" is a continuous fragrance-imparting component-emitting fiber optionally containing antimicrobial agent.

FIG. 1G is a cutaway side elevation view (in schematic form) of an extruded by-component fiber, which is a so-called "island-in-the-sea" fiber with a substantially cross sectional shape showing four a polymer islands having substantially circular cross sections, with the polymer islands having embedded therein fragrance and, optionally, antimicrobial agent.

FIG. 1H is a diagrammatic and schematic representation of a method of producing a non-woven fabric laminate useful in the practice of our invention.

FIG. 1I is an enlarged, detailed isomeric view of a portion of the non-woven textile laminate produced according to the process of FIG. 1H.

FIG. 1J is a cross sectional view of the laminate of FIG. 1I taken along line 6003—6003 of FIG. 1I with the thickness of the face layer exaggerated.

FIG. 1K is a cross sectional view of another embodiment of the textile laminate of FIG. 1I with the thickness of the face layers exaggerated.

FIG. 1L is an exploded, detailed isomeric view of the textile laminate of FIG. 1I.

FIG. 1M is an isometric view of the non-woven fabric of FIG. 1L.

FIG. 7A is a photomicrograph of the controllably releasable or permanently fragrance-emitting dry or wet wipe laminar fabric article of our invention (1,000× magnification).

FIGS. 7B and 7C are photomicrographs of the controllably releasable or permanently fragrance-emitting dry or wet wipe laminar fabric article of our invention (200× magnification).

FIG. 7D is a photomicrograph of the controllably releasable or permanently fragrance-emitting dry or wet wipe laminar fabric article of our invention (200× magnification).

FIG. 7E is a photomicrograph of the controllably releasable or permanently fragrance-emitting dry or wet wipe laminar fabric article of our invention (500× magnification).

DETAILED DESCRIPTION OF THE DRAWINGS

Figure 4:
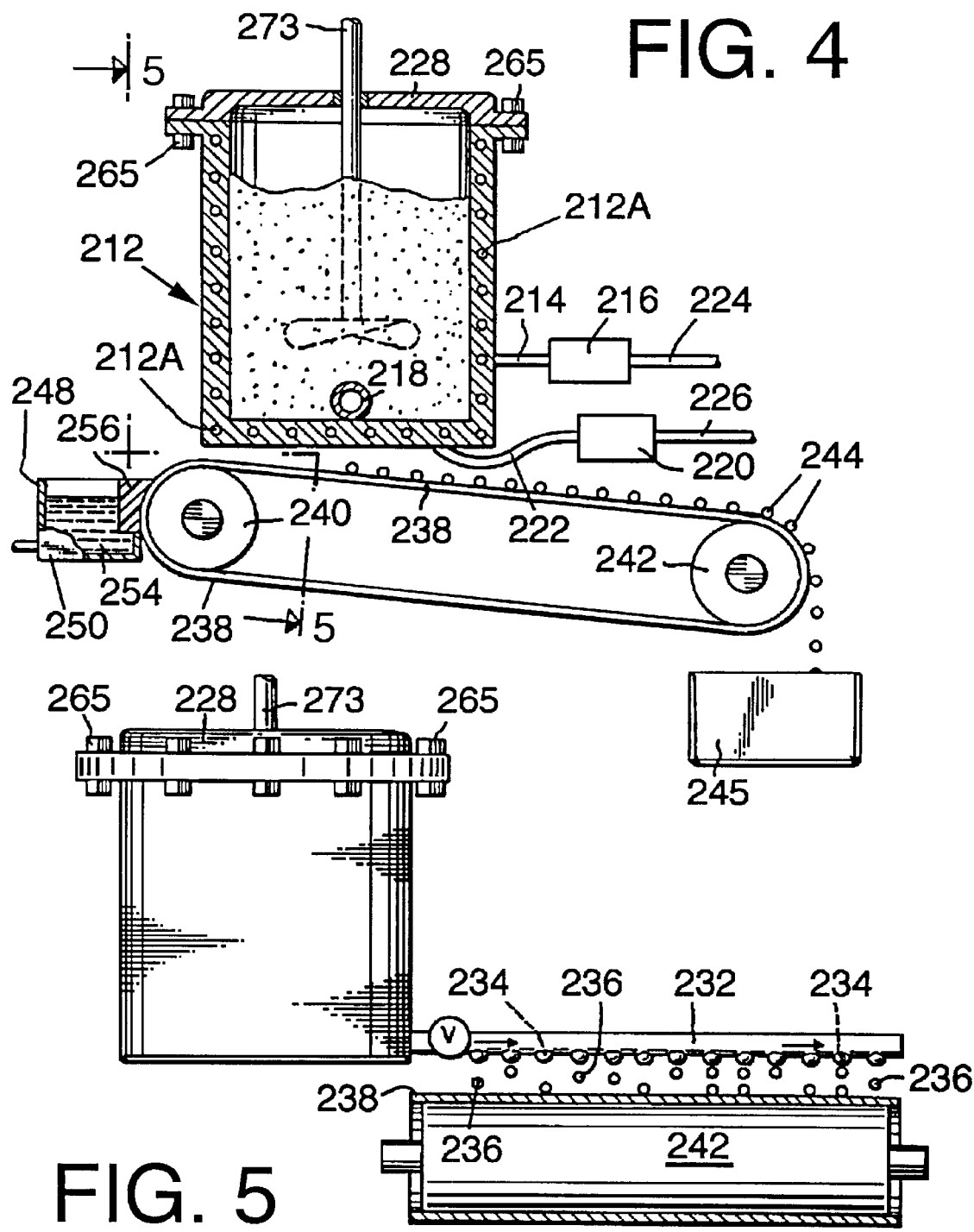
FIG. 4 represents a cutaway side elevation view of apparatus used in forming perfumed polymers which contained embedded in the interstices thereof at least one fragrance component which is emitted from one or more continuous fragrance-imparting component-emitting fibers optionally containing antimicrobial agent.
Figure 5:
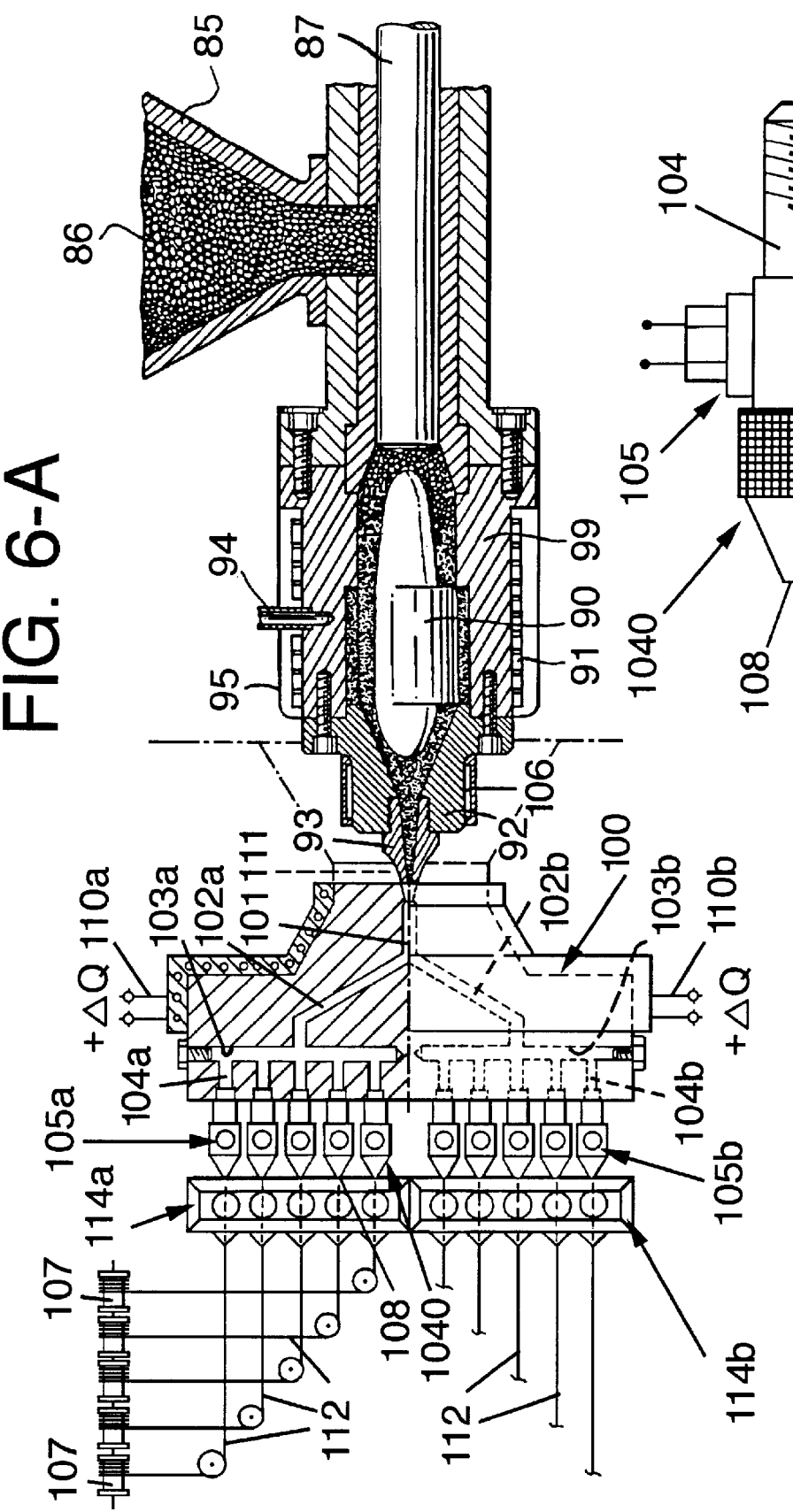
FIG. 5 is a front view of the apparatus of FIG. 4 looking in the direction of the arrows along the lines 5—5 of FIG. 4.

Referring to FIG. 1A, microporous polymer particles containing fragrance components in the interstices thereof at a location indicated by reference numeral 31, prepared according to processes as shown in FIGS. 4 and 5 of U.S. Pat. No. 5,300,489 and described in the Detailed Description of the Drawings thereof at column 2, lines 58–68, at column 3, lines 1–68 and at column 4, lines 1–13, are heated using heating means 33 to form a melt. The melt is admixed with polypropylene (nonscented) from location 32 heated by heating means 34. The mixing takes place in mixing vessel 37 (e.g., a Banbury mixer). The microporous polymer melt is passed through line 36 into mixer 37, and the polypropylene melt is passed through line 35 into mixer 37. The resulting mixture is then passed through line 38 into a thread extruder (of the type shown in FIG. 6A) whereby fibers containing controllably releasable fragrance are produced. Simultaneously, non-woven fabric is produced at location 41 and conveyed via conveyor 43 to location 42.

The thread produced from thread extruder 39 is conveyed via conveyor 40 to location 44 whereat the fiber is needle punched into the non-woven cloth from location 42. The needle punching may be effected according to the procedure of U.S. Pat. No. 5,902,757 issued on May 11, 1999, the specification for which is incorporated by reference herein. The resulting product is conveyed to location 45 where it is cut into convenient-to-use dry wipe or wet wipe articles.

Referring to FIG. 1B, microporous fragrance particles produced according to the procedure as set forth at column 2, lines 58–68, at column 3, lines 1–68 and at column 4, lines 1–13 of U.S. Pat. No. 5,300,489 (incorporated herein by reference) is conveyed from location 46 to vessel 47 where it is heated using heating element 48. The resulting product is conveyed to thread extruder 49 (as shown in detail in FIG. 6A, described, infra) Simutaneously, non-woven fabric is produced at location 50 (for example, using the process of PCT Application No. 99/22059 published on May 6, 1999, the specification for which is incorporated by reference herein). The non-woven fabric is conveyed to location 51 and then to location 52 where it is needle punched with the extruded fiber from location 49. The resulting product is then conveyed to location 53 where it is cut into usable dry wipe or wet wipe articles.

Referring to FIG. 1C, microporous articles containing controllably releasable fragrances are prepared at location 30 (in accordance with, for example, the processes described in U.S. Pat. No. 4,542,162 issued on Sep. 17, 1985, the specification for which is incorporated by reference herein). The resulting product is conveyed into apparatus 31 where it is melted using heating means 33. The resulting fragrance-containing melt is conveyed via conveyor 36 into mixing vessel 37 where the melt is mixed with polypropylene. The polypropylene (in the absence of fragrance) is melted at location 32 using heating means 34. The non-fragranced polypropylene is also conveyed into mixing vessel 37 via conveyance means 35. The resulting product, after mixing in vessel 37, is conveyed into thread extruder 39 via conveyance means 38 whereupon controllably releasable fragrance-emitting fibers are formed. Simultaneously, non-woven fabric is produced at location 41 (according to, for example, the processes set forth in PCT Application 98/51850 published on Nov. 19, 1998, the specification for which is incorporated by reference herein) and conveyed via conveyance means 43 to location 42. The resulting non-woven fabric is then conveyed to location 44 where it is needle punched with fragrance-emitting fiber from location 39 conveyed via conveyance means 40 to location 44. The needle punching operation is carried out in accordance with the processes such as that set forth in U.S. Pat. No. 5,902,757 issued on May 11, 1999, the specification for which is incorporated by reference herein. The resulting article in the form of a lamina of non-woven fabric having woven therethrough fragrance-emitting fiber is conveyed to location 54 where it is heated using heating means 55. The resulting heated article is then passed through a roller press 56 where the fibers containing the controllably releasable fragrance are sealed in place. The resulting product is conveyed to location 57 where the resulting articles of our invention are cut into convenient shapes for use as wet wipes or dry wipes. Alternatively, the laminae containing the fragrance-emitting fiber woven therethrough may be passed directly to a hot roller press 58, heated used heating means 59. The resulting product is then conveyed to location 57 where it is conveniently cut into articles useful as dry wipes or wet wipes.

Referring to FIG. 1D, microporous polymer particles containing controllably releasable fragrances and optionally antimicrobial agent prepared at location 46 according to, for example, the process set forth at columns 2, 3 and 4 of U.S. Pat. No. 5,300,489 issued on Apr. 5, 1994, the specification for which is incorporated by reference herein, are conveyed to location 47 where the particulate material is heated using heating means 48 whereby a melt is formed. The resulting fragrance-emitting melt is conveyed into fiber extruder 49 where fragrance-emitting fibers are produced. An example of such a fiber extruder is set forth in FIG. 6A, described in detail, infra. The resulting fragrance-emitting fiber (which optionally emits antimicrobial agent in addition in a controlled release manner) is conveyed to location 52. Simultaneously, non-woven fabric prepared at location 50 is conveyed to location 51 and then to location 52 where it is needle punched with the fragrance-emitting fiber prepared at location 49. The needle punching is in accordance with such processes as the one set forth in detail in U.S. Pat. No. 5,902,757 issued on May 11, 1999, the specification for which is incorporated by reference herein. The resulting lamina, which is a non-woven article having woven therethrough fragrance-emitting fiber, is conveyed to location 60 where it is heated using heating means 61. The resulting heated lamina, having woven therethrough fragrance-emitting fiber, is then conveyed to roller press 62 where the fragrance-emitting fibers are firmly fixed in place. The temperatures at locations 60 and 62 and the heat input energy at locations 60 and 62 are such that although the fiber is made to be firmly in place in the non-woven fabric lamina, the fragrance (and optionally antimicrobial agent) contained in the fiber is not to any substantial extent prematurely released. The resulting product is then conveyed to location 63 where it is cut into convenient dry wipe or wet wipe articles. In the alternative, the non-woven fabric lamina having fragrance-emitting fiber woven therethrough is passed directly from location 52 through hot roller press 64, heated using heating means 65 where the fibers are fixed in place. From the hot roller press, the resulting article is conveyed to location 63 where it is conveniently cut into useful wet wipe or dry wipe articles.

Referring to FIG. 1E, FIG. 1E is a schematic diagram showing apparatus for manufacturing a non-woven fabric useful in the practice of our invention. The method is also set forth in PCT Application No. 99/22059 published on May 6, 1999, the specification for which is incorporated by reference herein. Shown is apparatus for producing a non-woven material by hydroentangling a fiber mixture containing continuous filaments, e.g., melt-blown and/or spun-bond fibers and natural fibers and/or synthetic staple fibers. The method is characterized by foam forming a fibrous web 2014 of natural fibers and/or synthetic staple fibers and hydroentangling together the foamed fiber dispersion with the continuous filaments 2011 for forming composite material where the continuous filaments are well integrated with the rest of the fiber. The hydroentangling is carried out at location 2016, and the produced non-woven fabric is indicated by reference numeral 2024. More specifically, the foam is sucked through the wire 2012 and down through the web of melt-blown fibers laid on the wire by means of suction boxes arranged under the wire. The integrated fibrous web of melt-blown fibers and other fibers is hydroentangled while it is still supported by the wire 2012 and forms a composite material 2024. Possibly, the fibrous web can, before hydroentangling, be transferred to a special entangling wire, which possibly can be patterned in order to form a patterned non-woven fabric. The entangling station 2016 can include several rows of nozzles from which very fine water jets under very high pressure are directed against the fibrous web to provide an entangling of the fibers. During the process, a foam-formed fibrous web 2014 from a head box 2015 is laid on top of the melt-blown layer. "Foam forming" means that a fibrous web is formed from a dispersion of fibers in a foamed liquid-containing water and a tenside. Such foam-forming technique is described in U.S. Pat. No. 4,443,297, the specification for which is incorporated by reference herein. Through the intensive foaming effect, there will already at this stage occur a mixing of the melt-blown fibers with the foamed fiber dispersion. Air bubbles from the intensive turbulent foam that leaves the head box 2015 will penetrate down between and push apart the movable melt-blown fibers so that the somewhat coarser foam-formed fibers will be integrated with the melt-blown fibers. Thus, after this step, there will mainly be an integrated fibrous web and no longer layers of different fibrous webs.

Referring to FIG. 1F, a stitch-bonded, non-woven fabric sheet 3010 has a felt web 3012 with hydrophobic layer 3014 and a hydrophilic layer 3016 stitch bonded with a fragrance-emitting fiber 3018' and 3018" and 3018 to create fiber faces (3024 and 3026) over the respective outer surfaces (3020 and 3022) of the non-woven felt web (3012). Sheet 3010 may be used as a fluid-retention non-woven fabric such as to replace the facing fabric and felt layer in the wet wipe or dry wipe article of our invention. As stated, supra, the fragrance-emitting fiber 3018 (prepared using the apparatus of FIG. 6A, hereinafter described in detail, infra) were prepared using the process of PCT Application No. 99/20565 published on Apr. 29, 1999 (incorporated herein by reference) may also contain controllably releasable antimicrobial agent.

Referring to FIG. 1G, FIG. 1G shows an extruded synthetic fiber according to an exemplary embodiment of the invention of PCT Application No. 99/21507 published on May 6, 1999, the specification for which is incorporated by reference herein (International Application No. PCT/US 98/22810 filed on Oct. 28, 1998). In FIG. 1G, an extruded by-component fiber 4010 is a so-called "island-in-the-sea" fiber with a substantially circular cross-sectional shape. Specifically, fiber 4010 comprises a durable "sea" circular cross-sectional shape. Specifically, fiber 4010 comprises a durable "sea" polymer 4012 which forms the bulk of fiber 4010 and four polymer "islands" 4014 having substantially circular cross sections. The polymer islands 4014 are embedded in the sea polymer 4012 and lie along the outer surface of fiber 4010 spaced apart by approximately 90° such that the islands 4014 are not totally encapsulated by the sea polymer 4012 and a portion of the outer surface of fiber 4010 is formed by the polymer islands 4014. The sea polymer 4012 of fiber 4010 may be made from any organic high polymer such as nylon, polyethylene, terephthalate or polypropylene or copolymers of propylene and ethylene or copolymers of propylene and vinyl acetate. The polymer islands 4014 are composed of a polymer such as a copolymer of ethylene and vinyl acetate containing controllably releasable fragrance and optionally containing antimicrobial agent.

Referring to FIGS. 1H, 1I, 1J, 1K, 1L and 1M, these Figures all relate to a non-woven textile laminate comprising a fiberfill web substrate and face layer as described in detail in U.S. Pat. No. 5,925,581 issued on Jul. 20, 1999, the specification for which is incorporated herein by reference. Thus, the textile laminate is indicated generally by reference numeral 6010. The formation of the textile laminate 6010 is illustrated in FIGS. 1H and 1I. A fiber-filled substrate 6020 is formed from first fibers 6021 at an offline or online formation station using conventional techniques such as cross-lapped card web, inline laid card web, corrugated card web, air laid web, needle tacked air laid web, sliver knit, flannel, brushed woven or knitted fabric, velour, flocked substrate and the like, the selection of which is well within one having ordinary skill in the art. The fiber-filled web substrate 6020 is transported from the formation station using a continuous foraminous belt 6023 mounted on rollers 6024a, 6024b, 6024c, 6024d and 6024e for movement to a fiber extrusion station 6027. It is noted that the partially closed nip between rolls 6024c and 6024d contributes to the mechanical interentanglement. It is further noted that rolls 6024a and 6024b may comprise a single perforated cylinder, and the roll 6024b may further comprise a source of negative air pressure whereby the second fibers 6030 are drawn toward and into the fiberfill web substrate 6020. Further, the continuous foraminous belt 6023 may be threaded in a non-folded, planar manner such that rolls 6024a, 6024d and 6024e provide mechanical suspension only, while a source of negative air pressure of equivalent functions as perforated cylinder roll 6024b is supplied by a transverse manifold or plenum, and the calibrating nip or working action between rolls 6024c and 6024d may be provided in a conventional manner. The fiber diameter for meltblown-spunbonded species 6031 is very fine relative to the fiber diameter of the cross-lapped card web (fiberfill web substrate). The extruded fibers also can comprise partially oriented filaments which are easily drafted by application of mechanical force such as would be supplied by the nip between rolls 6024c and 6024d.

At the fiber extrusion station 6027, an extruder 6029 extrudes the second fibers 6030 as a fiber stream 6031 to provide a face layer 6035. Such fiber stream may also include antimicrobial agents as well as fragrance agents and would act as an additional control release supplying source of fragrance material and/or antimicrobial material in addition to the fiber that is woven through the non-woven fabric. The extruded fibers preferably are meltblown thermoplastic polymer microfibers of polypropylene, polyamides (e.g., nylon 6, nylon 66), polybutylene terephthalate, polyethylene, polyethylene terephthalate, linear low density polyethylene and copolymers and blends thereof. Typically, meltblown fibers have a finer linear density of about 0.05 to 5 denier per filament. The extruded meltblown fibers are prepared using conventional techniques such as described in U.S. Pat. No. 3,978,185, Buntin, et al, the disclosure of which is incorporated herein by reference in its entirety and *Industrial and Engineering Chenistry*, Volume 48, No. 8 (1965) at pages 1342–1356. Generally, the process involves extruding one of the thermoplastic fibers listed above through orifices (often about 34 orifices per linear inch) of a heated nozzle into a stream of hot gas or air, preferably having a controlled density to attenuate the molten resin as fibers. The temperature of the hot gas or air is typically greater than ambient temperature, but is less than the die temperature. Thus, the fibers are quenched by the hot gas or air. A particularly preferred meltblown fiber is polypropylene such as EXXON ESCORENE® 500 melt flow rate polypropylene available from Exxon Chemical Company of Houston, Tex.

The same thermoplastic fibers can also be extruded using spunbonding techniques such as described, for example, in U.S. Pat. Nos. 3,338,992 and 3,341,394 to Kinney, the disclosures of which are incorporated herein by reference in their entirety. Generally, the spunbonding process involves continuously extruding one of the thermoplastic fibers through a spinneret to form discrete filaments. The filaments are drawn to achieve molecular orientation and tenacity. Typically, spunbonded fibers have a coarser linear density of about 1 to 20 denier per filament. One having ordinary skill in the art will recognize that other extrusion techniques can be used, and that meltblown and spunbonded technology sometimes overlap.

The extruded second fibers 6030 are laid onto the fiberfill web substrate 6020 under conditions sufficient to mechanically interentangle with the first fibers 6021 of the fiberfill web substrate 6020. Typically, this is accomplished by providing sufficient negative draft under the fiberfill web substrate 6020 and by controlling the extruder die to collector (substrate 6020) distance. The extruded second fibers tend to dither or whip back and forth on exit of the orifice or spinneret due to air turbulence. This contributes to the tendency of the second fibers to mingle among themselves and to form a web of considerable integrity prior to contact with the fiberfill web substrate 6020, and thereafter, to penetrate into and have an affinity for the fiberfill substrate and to provide mechanical interentanglement. This mechanical entanglement is illustrated in FIGS. 1J and 1K. The mechanical interentanglement is comparable to VELCRO®-type entanglement in that the different fibers tend to act similarly to the hooks and loops of VELCRO®. This controlled clinging or adherence can also be used to facilitate bonding of a decorative cover layer to form a textile laminate for the wet wipe or dry wipe articles of our invention.

The extruder die to substrate (collector) distance can be used to control the texture of the fiber stream 6031 of the extruded second fibers 6030 so that the outer surface of the fiber stream 6031 on the textile laminate 6010 can be made to have either greater or less tendency to cling to other plies of textile laminate 6010, as may occur when textile laminate 6010 having only one face layer 6035 is stored in a rolled and compressed configuration. Shorter than conventional extruder die to substrate (collector) distance has been found to enhance this polishing or sealing of face layer 6035 so that storage in compressed roll form is practicable (even with additional fiber woven therethrough). Further, the degree of clinging between face layer 6035 and supplemental materials such as decorative cover sheets that are applied to textile laminate 6010 can be controlled in this way.

Albeit even lighter webs of extruded second fibers 6030 can be made which are too weak to be handled as separate and independent webs, these webs also contribute desirable properties to the textile laminate 6010 when combined in the exemplary manner with a fiberfill web substrate 6020.

It is noted that there is some thermal or fusion bonding of the first fibers 6021 and the extruded second fibers 6030 inasmuch as thermoplastic fibers are often used. Additionally, a face layer 6035 and a base layer 6036 can be either simultaneously in a single machine operation or in separate lines laid onto the fiberfill web substrate 6020. Additionally the face layer 6035 and base layer 6036 can be formed from the same or different fibers listed previously.

The textile laminate 6010 can be used in a variety of embodiments. Generally, the textile laminate 6010 is used for its encapsulating properties (that is, encapsulating additional fragrance and/or antimicrobial agent), its resilient bulk properties or its tensile strength. As shown in FIGS. 1L and 1M, the textile laminate 6010 can be used in a dry wipe as the layer providing loft. Outer layers 6040a and 6040b of dry wipe material are sewn around the textile laminate.

Figure 2:
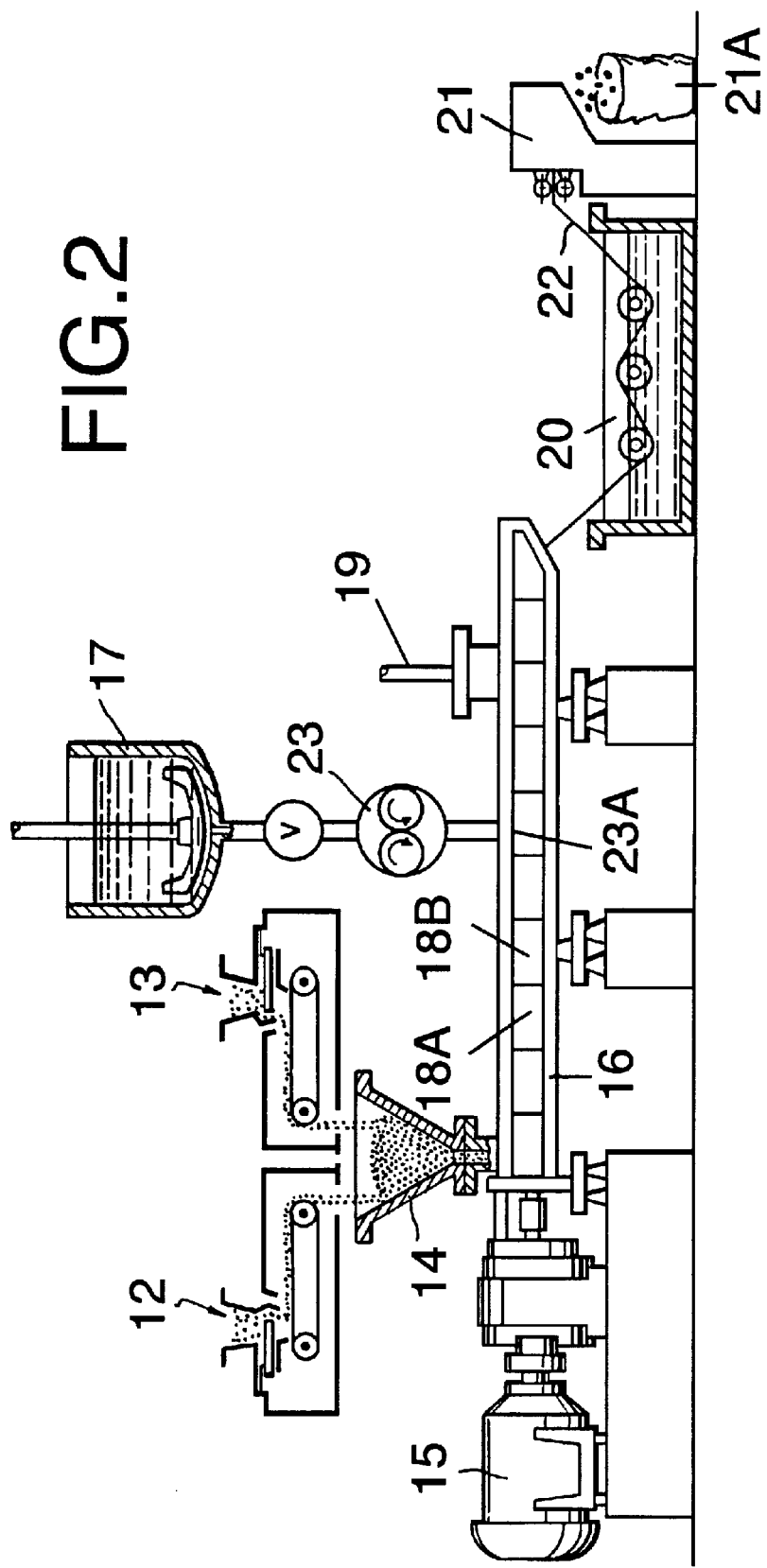
FIG. 2 is a cutaway side elevation, schematic diagram of a screw extruder during the compounding of the resin with the solid or liquid fragrance (with optional antimicrobial agent) while simultaneously adding foaming agent into the hollow portion of the barrel of the extruder and incorporates pelletizing apparatus used in pelletizing the extruded foamed tow produced as a result of the extrusion operation.

FIG. 2 is a schematic cutaway elevation diagram of the extrusion and pelletizing apparatus useful in carrying out a process for producing polymer matrix particles having releasably entrapped therein at least one aroma-imparting component in a concentration of from about 1% up to about 45% by weight of the polymer particles and, optionally, one or more antimicrobial substances.

Motor 15 drives the extruder screws located at 23A in barrel 16, the extruder being operated at temperatures in the range of about 150° C. up to about 250° C. At the beginning of the barrel, resin at source 12 together with additives, e.g., antimicrobial agents, processing aids and densifiers at location 13 is added via addition funnel 14 into the extruder. Simultaneously (when the operation reaches "steady state"), functional fluid or solid is added to the extruder at one, two or more of barrel segments 3–8 of the extruder (which may be a twin screw or single screw extruder) at locations 18a, 18b, 18c and 18d by means of gear pump 23 from source 17. From source 19 into barrel segments 5–10, the gaseous or liquid blowing agents, e.g., nitrogen, carbon dioxide and the like, are added simultaneously with the addition of functional fluid (fragrance and, optionally, antimicrobial agents) or solid (fragrance and, optionally, antimicrobial agent). The feed rate range of resin is about 80–300 lbs per hour. The feed rate range of the functional solid or liquid is between 1% and 35% of the feed rate range of the resin. The blowing agent rate range is such that the pressure of the gas or the pressure over the liquid being fed into the extruder is between about 50 and 200 psig. If desired, the extruded ribbon or cylinder may be passed through water bath 20 and pelletizer 21 into collection apparatus 21a.

Figure 3:
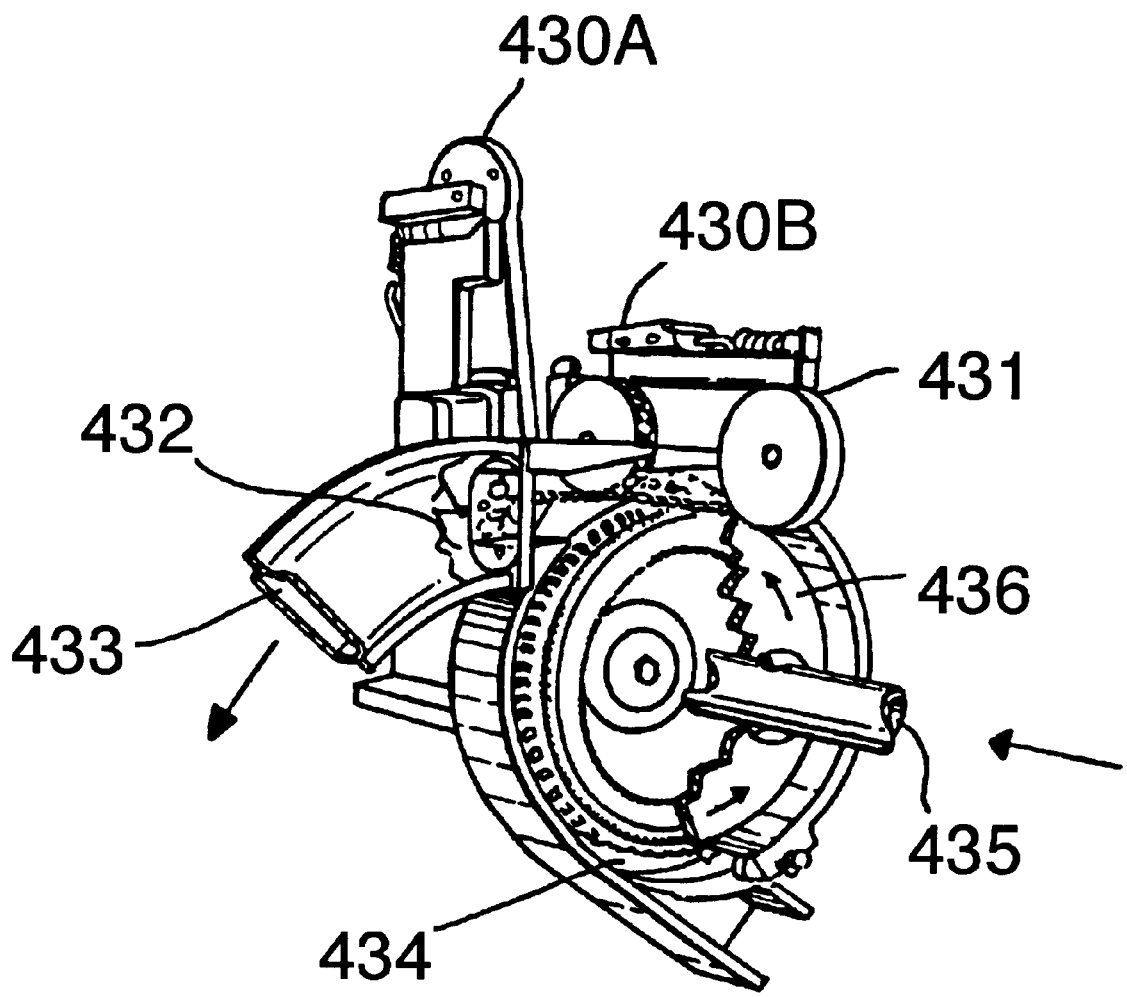
FIG. 3 is a cutaway perspective diagram of a pelletizing apparatus used in conjunction with the extrusion apparatus; for example, that illustrated in FIG. 2 whereby the extruded tow is pelletized.

FIG. 3 is a detailed cutaway perspective view of such a pelletizer as is used in conjunction with the apparatus of FIG. 2. The extruded material coming from the water cooler which is already foamed and which already contains functional fluid or solid is fed into the pelletizer at zero pressure at location 434. The pelletizer is operated using a spinning extrusion die 436 and operated by means of a rotating wheel 434. Moving pellet knife 431 and dual knife units 430a and 430b cause pellets to be formed which fly into a cooling water stream 432. The resulting pellets which are foamed and contain functional solid or liquid exit from the pelletizer 433.

The fragrance-emitting polymer matrix particles having releasably entrapped therein at least one aroma-imparting component in a concentration of from about 1% up to about 45% can also be prepared according to the apparatus shown in FIGS. 4 and 5. Now referring to FIGS. 4 and 5, there is provided a process for forming scented polymer pellets (which also may contain, optionally, antimicrobial agent) (wherein the polymer may be a thermoplastic polymer such as low density polyethylene or polypropylene or copolymers of ethylene and vinyl acetate or mixtures of polymers and copolymers such as copolymers of ethylene and vinyl acetate and, in addition, polyethylene) such as pellets useful in the formation of plastic particles useful in fabricating the wet wipes and dry wipes of our invention. This process comprises heating the polymer or mixture of polymers to the melting point of said polymer or mixture of polymers, e.g., 250° C. in the case of low density polyethylene. The lower most portion of the container is maintained at a slightly lower temperature, and the material in the container is taken off at such location for delivery through the conduit. Thus, referring to FIGS. 4 and 5, in particular, the apparatus used in producing such elements comprises a device for forming the polymer containing perfume, e.g., polyethylene or polyethylene/polyvinyl acetate or mixtures of same or polypropylene, which comprises a vat or container 212 into which the polymer taken alone or in admixture with other copolymers and the perfuming substance and, optionally, the antimicrobial substance is placed. The container is closed by means of an airtight lid 228 and clamped to the container by bolts 265. A stirrer 273 traverses the lid or cover 228 in an airtight manner and is rotatable in a suitable manner. A surrounding cylinder having heating coils 212A which are supplied with electric current through cable 214 from a rheostat or control 216 is operated to maintain the temperature inside the container 212 such that the polymer in the container will be maintained in a molten or liquid state. It has been found advantageous to employ polymers at such a temperature that the viscosity will be in the range of 90–100 Saybolt seconds. The heater 218 is operated to maintain the upper portion of the container 212 within a temperature range of, for example, 220–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220–270° C.

Thus, the polymer or mixture of polymers added to the container 212 is heated from 10–12 hours, whereafter the perfume composition or perfume material (and, optionally, antimicrobial material) is quickly added to the melt. Generally, about 10–45% by weight of the resulting mixture of the perfumery substance (taken together, optionally, with antimicrobial agent) is added to the polymer.

After the perfume material (and, optionally, antimicrobial agent) is added to the container 212 the mixture is stirred for a few minutes, for example, 5–15 minutes, and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so the liquid polymer in intimate admixture with the fragrances (and, optionally, antimicrobial agent) will continuously drop through the orifices of 234 downwardly from the conduit 232. During this time, the temperature of the polymer intimately admixed with the perfumery substance (and, optionally, antimicrobial agent) in the container 212 is accurately controlled so that a temperature in the range of from about 240–250° C., for example (in the case of low density polyethylene), will exist in the conduit 232. The regulation of the temperature through the controls 216 and 220 is essential in order to insure temperature balance to provide for the continuous dropping or dripping of molten polymer intimately admixed with the perfume substance (and, optionally, antimicrobial agent) through orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid in order to insure the rapid cooling of each of the pellets 244. The pellets 244 are then collected from the container 250 and utilized for formation into the thread as shown, for example, in FIG. 6A.

Figure 6:
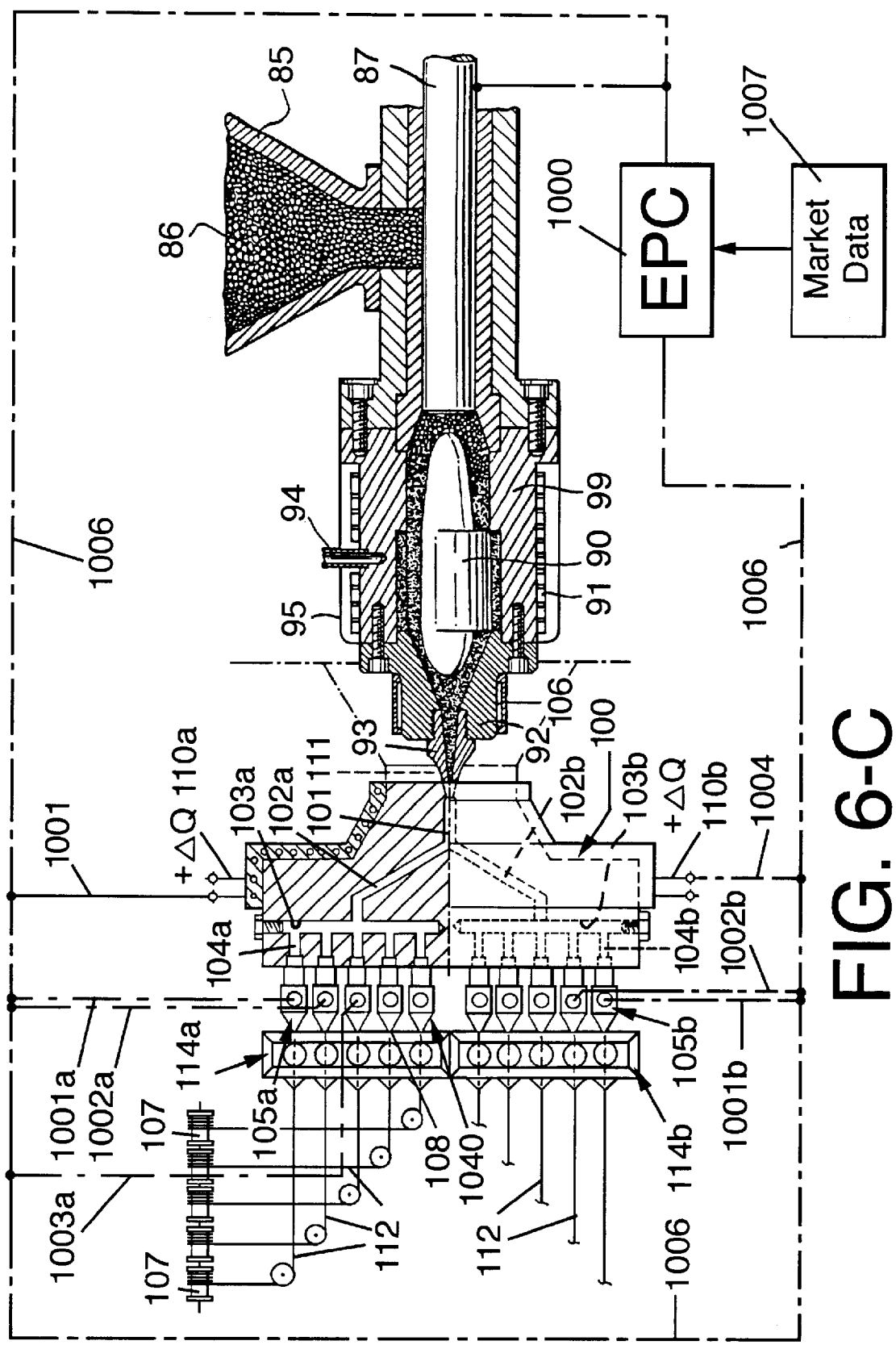
FIG. 6A shows the entirety of the cutaway side elevation view of injection molding apparatus with the hot runner system attached to the injection molding device and showing the entire operation for forming the continuous fragrance-imparting component-emitting fibers optionally containing antimicrobial agent useful in the practice of our invention.
FIG. 6B is an enlarged view of an adjustable nozzle wherein the fiber tow exits from the hot runner system portion of the injection molding apparatus.
FIG. 6C shows the injection molding/fiber-forming apparatus of our invention with electronic data processing controlling apparatus for computerized control of the fiber-foaming process aspect-of our invention.

Referring to FIGS. 6A and 6B, molding mix containing foamed or non-foamed polymeric particles 86 is fed into a plasticizing cylinder through hopper 85. When the mold opens, the cylinder plunger 89 moves back permitting material to drop into the cylinder. On the closing stroke, the mold members lock tightly together, and the cylinder plunger moves forward forcing the newly delivered material from the hopper into the heating zone of the cylinder 90. The polymeric particles 86 already contain fragrance and, optionally, antimicrobial agent. This material in turn displaces a "shot" of molten material through the nozzle 93 into the thread-forming part of the apparatus through orifice 111. The apparatus shown by reference numeral 100, in general, is a "hot runner" system as manufactured by Ewikon N. A. Incorporated of 665 Tollgate Road, Station "F,"Elgin, Ill. 60123. The entry part of the hot runner system of the apparatus of FIG. 6A is through port 101. The block is heated using heating elements 110a and 110b. Entry port 101 diverges into two streams, 102a and 102b. In turn, the two lines in the hot runner system, 102a and 102b, further diverge into a number of additional lines (shown as five lines each, indicated by reference numerals 104a and 104b) through manifolds indicated by reference numerals 103a and 103b. At the exits of the "hot runner" system are exit valves indicated by reference numerals 105a and 105b, which are usually controlled via electronic data processing systems. A detail enlarged drawing of an exit valve system is set forth in FIG. 6B. The actual controlling valve is indicated by reference numeral 105, a remote control valve. The overall exit port is indicated by reference numeral 104. The actual exit orifice is indicated by reference numeral 108 (a "adjustable" nozzle for fiber diameter variation). The adjustment of the nozzle is made through adjusting mechanism 108a. The fibers pass through cooling chambers indicated by reference numerals 114a and 114b. The cooled fiber containing controllably releasable fragrance and, optionally, controllably releasable antimicrobial agent is shown by reference numeral 112 and is wound up on a spool indicated by reference numeral 107 for subsequent use in weaving the fiber or needle punching the fiber through the non-woven laminar fabric article.

Figure 7:
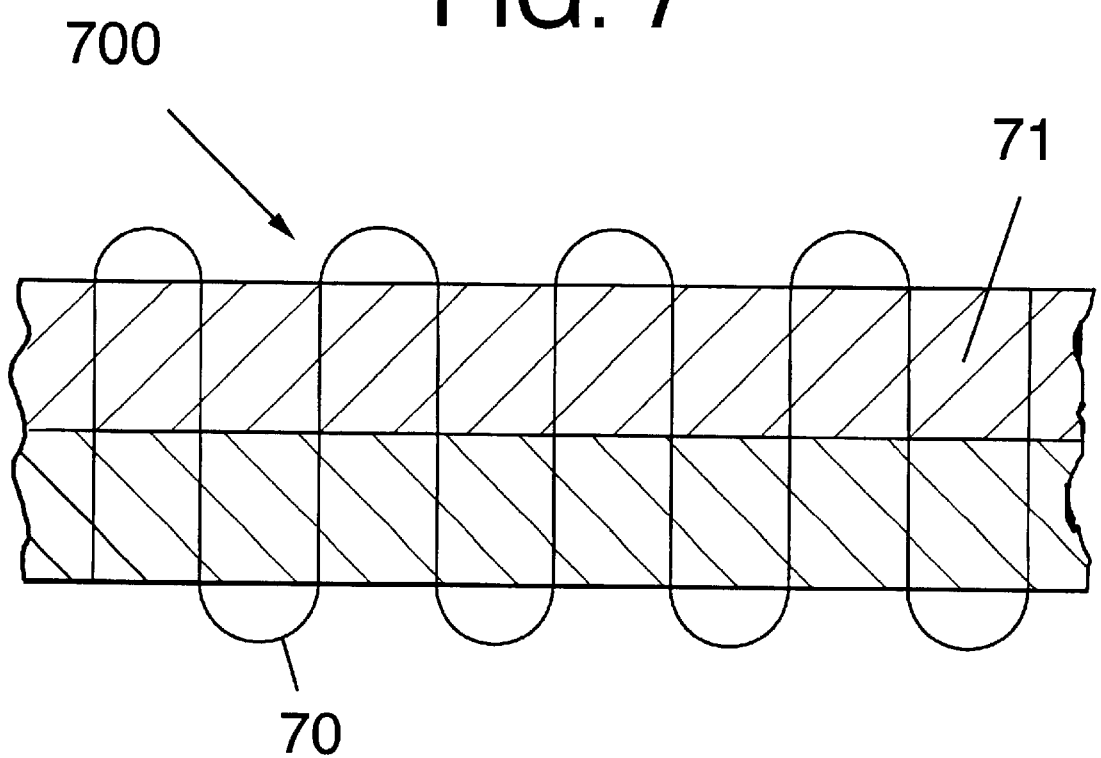
FIG. 7 is a cutaway side elevation view of stitch bonded, non-woven fabric of our invention showing the stitch bonding with the continuous fragrance-imparting component-emitting fiber optionally containing antimicrobial agent of our invention.

Now referring to FIG. 7, FIG. 7 sets forth a simplified cutaway side elevation view of a cross section of the wet wipe or dry wipe article of our invention. Reference numeral 71 shows a non-woven fabric layer of the type produced according to U.S. Pat. No. 5,925,581 issued on Jul. 20, 1999, the specification for which is incorporated by reference herein. Reference numeral 70 indicates the fiber produced using the apparatus of, for example, FIGS. 6A and 6B. The fiber is needle punched or woven through the layers of non-woven fabric 71. The overall article is indicated by reference numeral 700. FIGS. 7A, 7B, 7C, 7D and 7E set forth photomicrographs of the wet wipe or dry wipe article of our invention. Reference numeral 710 sets forth the photomicrographs in general. The fiber indicated by reference numeral 70 is the fragrance-emitting (and, optionally, antimicrobial agent-emitting) fiber produced using the apparatus, for example, of FIGS. 6A and 6B. Reference numeral 71 shows the fibers of the non-woven fabric produced, for example, according to the process of U.S. Pat. No. 5,925,581 issued on Jul. 20, 1999, incorporated herein by reference; or using the apparatus of PCT Application No. 99/22619 published on May 14, 1999, incorporated herein by reference; or using the process of U.S. Pat. No. 5,454,142 issued on Oct. 3, 1995 (title: "NON-WOVEN FABRIC HAVING ELASTOMETRIC AND FOAM-LIKE COMPRESSIBILITY AND RESILIENCE AND PROCESS THEREFOR"), incorporated herein by reference.

The following example sets forth means for preparing the dry wipe and wet wipe articles of our invention. All parts and percentages given herein are by weight unless otherwise specified.

EXAMPLE I (PART A)

PREPARATION OF FRAGRANCE FORMULATION

The following woody cologne perfume formulation is prepared:

| Ingredients | Parts by Weight |
|---|---|
| Bergamot oil | 150 |
| Orange oil | 200 |
| Lemon oil | 50 |
| Eugenol | 10 |
| 4-(4-Methyl-4-hydroxyamyl-$\Delta^3$-cyclohexene) carboxaldehyde (LYRAL ®, trademark of International Flavors & Fragrances Inc. of New York, New York) | 40 |
| Ylang oil | 2 |
| Petitgrain Paraguay | 10 |
| γ-Methylionone | 20 |
| Vetiver Venezuela | 18 |
| 3-α-Methyl-dodecahydro-6,6,9a-trimethylnaptho[2,1-b]furan | 50 |
| Product produced by the reaction of acetic anhydride, polyphosphoric acid and 1,5,9-trimethyl cyclododecatriene-1,5,9 according to the process of Example 1 of U.S. Letters Pat. No. 3,718,697, the specification for which is incorporated by reference herein. | 50 |
| 1-Ethoxy-4-(3'methylbutyl)cyclohexane prepared according to Example III of U.S. Letters Pat. No. 5,543,398, the specification for which is incorporated by reference herein. | 12 |

EXAMPLE I (PART B)

PREPARATION OF FRAGRANCE-CONTAINING MICROPOROUS POLYMER PARTICLES

Using the apparatus of U.S. Pat. No. 3,505,432 issued on Apr. 7, 1970 (the specification of which is incorporated herein by reference), 75 lbs of a 50:50 mixture of PCL-700 polyepsilon caprolactone (manufactured by the Union Carbide Corporation of New York, N.Y.) having a melting point of about 180–190° F.: low density polyethylene are heated to about 250° F. 25 Pounds of the fragrance formulation of (Part A) of this Example is then quickly added to the liquefied polymer mixture. 25 Pounds of the antimicrobial substance having the structure:

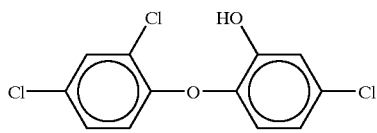

("triclosan) is then quickly added to the liquefied polymer mixture. The temperature is then raised to about 250° F. and the mixing is effected for 5–15 minutes. The molten polymer, enriched with fragrance and enriched with antimicrobial agent, is then formed into polymer beads or pellets. 50 Pounds of the scent containing "master pellets" are then added to 30 lbs of unscented polypropylene and the mass is heated into the liquid state.

The resulting liquid is formed into a continuous fiber (25 denier) using the apparatus of FIGS. 6A and 6B, described in detail, supra.

Separately, a non-woven fabric is prepared using the apparatus and process of U.S. Pat. No. 5,454,142 issued on Oct. 3, 1995 (entitled: "NON-WOVEN FABRIC HAVING ELASTOMETRIC AND FOAM-LIKE COMPRESSIBILITY AND RESILIENCE AND PROCESS THEREFOR), the specification for which is incorporated herein by reference. The non-woven fabric contains the following:

10% cellulose acetate fiber;

18% polypropylene; and

72% viscose.

The fragrance-emitting fiber produced using the apparatus of FIGS. 6A and 6B (described, supra) is then needle punched into the non-woven fabric in a ratio of 20 parts of fragrance-emitting fiber: 100 parts of non-woven fabric.

The resulting article is then passed through warm compression rollers maintained at 40° C. and the resulting product is used as a dry wipe.

What is claimed is:

1. A process for producing a fragrance-emitting laminar fabric article comprising the sequential steps of:

(a) providing one or more continuous fragrance-imparting component-emitting fibers optionally containing antimicrobial agent of from about 3 denier up to about 60 denier;

(b) providing a non-woven fabric laminar substrate;

(c) weaving said fragrance-imparting component-emitting fiber or fibers through said non-woven fabric laminar substrate across at least a major portion of the surface area of the non-woven fabric laminar substrate; and (d) optionally adding additional fragrance and/or antimicrobial agent to the resulting laminar fabric article.

2. A process for producing a fragrance-emitting laminar fabric article comprising the sequential steps of:

(a) providing one or more continuous fragrance-imparting component-emitting fibers optionally containing antimicrobial agent of from about 3 denier up to about 60 denier;

(b) providing a non-woven fabric laminar substrate;

(c) optionally adding additional fragrance and/or antimicrobial agent to the non-woven fabric laminar substrate; and (d) weaving said fragrance-imparting component-emitting fiber or fibers through said non-woven fabric laminar substrate across at least a major portion of the surface area of the non-woven fabric laminar substrate.

3. A process for producing a fragrance-emitting laminar fabric article comprising the sequential steps of:

(a) providing one or more continuous fragrance-imparting component-emitting fibers optionally containing antimicrobial agent of from about 3 denier up to about 60 denier;

(b) providing a non-woven fabric laminar substrate;

(c) optionally adding additional fragrance and/or antimicrobial agent to the resulting laminar fabric article;

(d) weaving said fragrance-imparting component-emitting fiber or fibers through said non-woven fabric laminar substrate across at least a major portion of the surface area of the non-woven fabric laminar substrate; and (e) optionally adding additional fragrance and/or antimicrobial agent to the resulting laminar fabric article.

4. A controllably releasable fragrance-emitting dry or wet wipe lamninar fabric article comprising a non-woven fabric lamina having woven therethrough and substantially throughout at least a finite portion of the laminar surface, at least one continuous tragrance-imparting component-emitting fiber which controllably and continuously releases fragrance at least for the time period of use of said dry or wet wipe laminar tabric article.

5. The process of claim 1 wherein the ratio of fragrance-emitting fiber:non-woven fabric lamina is from about 0.05:1 up to about 0.25:1.

6. The product of claim 4 wherein the weight:weight ratio of fragrance-emitting fiber:non-woven fabric lamina is from about 0.05:1 up to about 0.25:1.

7. The process of claim 1 wherein the continuous fragrance-imparting component-emitting fiber contains a fragrance which is also antimicrobial.

8. The process of claim 2 wherein the continuous fragrance-imparting component-emitting fiber contains a fragrance which is also antimicrobial.

9. The process of claim 3 wherein the continuous fragrance-imparting component-emitting fiber contains a fragrance which is also antimicrobial.

10. The fabric article of claim 4 wherein non-entrapped fragrance is included in the laminar fabric article.

11. A process for producing a fragrance-emitting laminar fabric article comprising the sequential steps of:
 (a) providing polymer matrix particles having releasably entrapped therein at least one aroma-imparting component which optionally has efficacious antimicrobial properties in a concentration of from about 1% up to about 45% by weight of the polymer particles and, optionally, one or more antimicrobial substances;
 (b) optionally admixing the matrix particles with a compatible polymer whereby a matrix polymer mixture is formed;
 (c) forming the polymer particles or the matrix polymer mixture into one or more continuous fragrance-imparting component-emitting fibers of from about 3 denier up to about 60 denier;
 (d) providing a non-woven fabric laminar substrate;
 (e) weaving said fragrance-imparting component-emitting fiber or fibers through said non-woven fabric laminar substrate across at least a major portion of the surface area of the non-woven fabric laminar substrate; and
 (f) optionally adding additional fragrance and/or antimicrobial agent to the resulting laminar fabric article.

12. A controllably releasable fragrance-emitting dry or wet wipe laminar fabric article which optionally has efficaciotis antimicrobial properties comprising a non-woven fabric lamina having woven therethrough and substantially throughout at least a finite portion of the laminar surface at least one continuous fragrance-imparting component-emitting fiber which controllably and continuously releases fragrance and, optionally, antimicrobial agent at least for a period of time of use of said dry or wet wipe laminar fabric article.

13. The process of claim 11 wherein the weight ratio of fiber:non-woven fabric is from about 0.05:1 up to about 0.25:1.

14. The product of claim 12 wherein the weight:weight ratio of fiber:non-woven fabric is from about 0.05:1 up to about 0.25:1.

15. The fabric article of claim 12 wherein non-entrapped fragrance is included in the article.

16. The article of claim 12 wherein non-entrapped antimicrobial substance is included in the article.

17. The article of claim 12 wherein the fragrance contained in the fragrance-imparting component-emitting fiber has antimicrobial properties.

18. A process for producing a fragrance-emitting laminar fabric article comprising the sequential steps of:
 (a) providing polymer matrix particles having releasably entrapped therein at least one aroma-imparting component in a concentration of from about 1% up to about 45% by weight of the polymer particles and one or more antimicrobial substances;
 (b) admixing the matrix particles with a compatible polymer whereby a matrix polymer mixture is formed;
 (c) forming the matrix polymer mixture into one or more continuous fragrance-imparting component-emitting fibers of from about 3 denier up to about 60 denier;
 (d) providing a non-woven fabric laminar substrate;
 (e) weaving said fragrance-imparting component-emitting fiber or fibers through said non-woven fabric laminar substrate across at least a major portion of the surface area of the non-woven fabric laminar substrate; and
 (f) adding additional fragrance and antimicrobial agent to the resulting laminar fabric article.

19. A controllably releasable fragrance-emitting dry or wet wipe laminar fabric article comprising a non-woven fabric lamina having Woven therethrough and substantially throughout at least a finite portion of the laminar surface at least one continuous fraganced-imparting component-emitting fiber which also contains antimicrobial agent and which controllably and continuously releases fragrance and antimicrobial agent at least for the time period of use of said dry or wet wipe laminar fabric article.

20. The process of claim 18 wherein the antimicrobial substance is selected from the group consisting of compounds defined according to the structures:

-continued

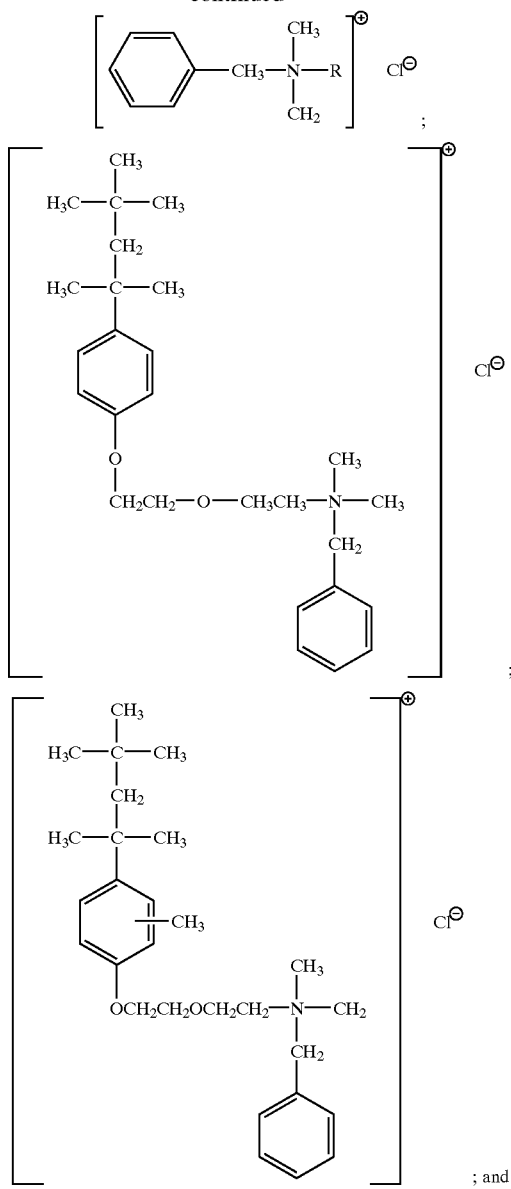
; and

-continued

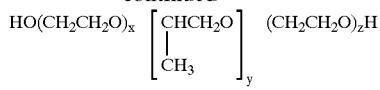

wherein the average values of x, y and z are, respectively, 75, 30 and 75 and wherein n is 0, 1 or 2.

21. The process of claim 18 wherein the ratio of fiber:non-woven fabric is from about 0.05:1 up to about 0.25:1.

22. The article of claim 19 wherein the weight:weight ratio of fiber:non-woven fabric is from about 0.05:1 up to about 0.25:1.

23. The article of claim 19 wherein non-entrapped fragrance and non-entrapped antimicrobial agent is present in the laminar fabric article.

24. The article of claim 4 wherein the continuous fragrance-imparting component-emitting fiber consists of fragrance and polypropylene and the non-woven fabric lamina consists essentially of cellulose acetate and viscose.

25. The article of claim 4 wherein the non-woven fabric lamina consists essentially of from about 5 up to about 20% by weight of cellulose acetate; from about 10 up to about 30% by weight of polypropylene; and from about 50 up to about 80% by weight of viscose.

26. The article of claim 25 which also includes antimicrobial agent having the structure:

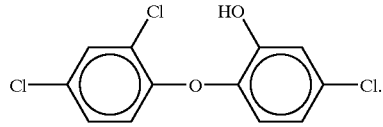

* * * * *